US006174862B1

(12) United States Patent
Brenneman

(10) Patent No.: US 6,174,862 B1
(45) Date of Patent: Jan. 16, 2001

(54) NEUROTROPHIC PEPTIDES OF ACTIVITY DEPENDENT NEUROTROPHIC FACTOR

(75) Inventor: Douglas E. Brenneman, Damascus, MD (US)

(73) Assignees: Ramot University Authority for Applied Research and Industrial Development, Ltd., Tel Aviv (IL); The United States of America as represented by the Department of Health and Human Services, Washington, DC (US)

(*) Notice: Under 35 U.S.C. 154(b), the term of this patent shall be extended for 0 days.

(21) Appl. No.: 08/324,297

(22) Filed: Oct. 17, 1994

Related U.S. Application Data

(63) Continuation-in-part of application No. 07/871,973, filed on Apr. 22, 1992, now Pat. No. 5,767,240, which is a continuation-in-part of application No. 07/688,087, filed on Apr. 22, 1991, now abandoned.

(51) Int. Cl.[7] .......................... A61K 38/08; A61K 38/10; A61K 38/17
(52) U.S. Cl. ................ 514/15; 514/12; 514/13; 514/14; 530/326; 530/327; 530/328; 530/324
(58) Field of Search .................. 514/12–15; 530/324, 530/326–328

(56) References Cited

U.S. PATENT DOCUMENTS 5,135,956 * 8/1992 Borg et al. .......................... 514/724

FOREIGN PATENT DOCUMENTS

WO 90/10449    9/1990    (WO).
WO 92/18140   10/1992   (WO).
WO 94/03208 * 2/1994    (WO).

OTHER PUBLICATIONS

Merck Manual, Fifteenth Edition, Merck & Co., Rahway, NJ (1987), see p. 1120.*
Venner et al., *Biochemica Biophysica Acta*, vol. 1087, pp. 336–338, 1990.*

* cited by examiner

*Primary Examiner*—Gary L. Kunz
*Assistant Examiner*—Stephen Gucker
(74) *Attorney, Agent, or Firm*—Townsend and Townsend and Crew LLP

(57) ABSTRACT

The present invention relates generally to Activity Dependent Neurotrophic Factor (ADNF). More particularly, the present invention relates to a family of polypeptides derived from ADNF that exhibit neuroprotective/neurotrophic action on neurons originating in the central nervous system and to uses thereof for the treatment of neurological deficiencies and for the prevention of cell death. The present invention also relates to pharmaceutical compositions designed to prevent neuronal cell death.

35 Claims, 12 Drawing Sheets

M. W.

66,000 →  —
45,000 → —

29,000 → —
24,000 → —

20,000 → —

14,000 → ●   ◄ ← ADNF 1    2

*FIG. 3C.*

SEQUENCE LISTING (1) GENERAL INFORMATION:

(iii) NUMBER OF SEQUENCES: 21

(2) INFORMATION FOR SEQ ID NO:1:

(i) SEQUENCE CHARACTERISTICS:
      (A) LENGTH: 14 amino acids
      (B) TYPE: amino acid
      (C) STRANDEDNESS:
      (D) TOPOLOGY: linear (ii) MOLECULE TYPE: peptide (xi) SEQUENCE DESCRIPTION: SEQ ID NO:1:

Val Leu Gly Gly Gly Ser Ala Leu Leu Arg Ser Ile Pro Ala
1               5                   10

(2) INFORMATION FOR SEQ ID NO:2:

(i) SEQUENCE CHARACTERISTICS:
            (A) LENGTH: 9 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:2:

Ser Ala Leu Leu Arg Ser Ile Pro Ala
1               5

(2) INFORMATION FOR SEQ ID NO:3:

(i) SEQUENCE CHARACTERISTICS:
            (A) LENGTH: 10 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:3:

Gly Ser Ala Leu Leu Arg Ser Ile Pro Ala
1               5                   10

(2) INFORMATION FOR SEQ ID NO:4:

(i) SEQUENCE CHARACTERISTICS:
            (A) LENGTH: 6 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:4:

Ser Ala Leu Leu Arg Ser
1               5

(2) INFORMATION FOR SEQ ID NO:5:

(i) SEQUENCE CHARACTERISTICS:
            (A) LENGTH: 8 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:5:

Ala Leu Leu Arg Ser Ile Pro Ala
1               5

(2) INFORMATION FOR SEQ ID NO:6:

(i) SEQUENCE CHARACTERISTICS:
            (A) LENGTH: 19 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:6:

Val Glu Glu Gly Ile Val Leu Gly Gly Gly Ser Ala Leu Leu Arg Ser
1               5                   10                  15

Ile Pro Ala (2) INFORMATION FOR SEQ ID NO:7:

(i) SEQUENCE CHARACTERISTICS:
            (A) LENGTH: 9 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:7:

Thr Ala Leu Leu Arg Thr Ile Pro Ala
1               5

(2) INFORMATION FOR SEQ ID NO:8:

(i) SEQUENCE CHARACTERISTICS:
            (A) LENGTH: 5 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:8:

Arg Ser Ile Pro Ala
1               5

(2) INFORMATION FOR SEQ ID NO:9:

(i) SEQUENCE CHARACTERISTICS:
            (A) LENGTH: 8 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:9:

Val Leu Gly Gly Gly Ser Ala Leu
1               5

(2) INFORMATION FOR SEQ ID NO:10:

(i) SEQUENCE CHARACTERISTICS:
            (A) LENGTH: 10 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:10:

Val Leu Gly Gly Gly Ser Ala Leu Leu Arg
1               5                   10

(2) INFORMATION FOR SEQ ID NO:11:

(i) SEQUENCE CHARACTERISTICS:
            (A) LENGTH: 12 amino acids
            (B) TYPE: amino acid
            (C) STRANDEDNESS:

```
            (D) TOPOLOGY: linear (ii) MOLECULE TYPE: peptide (xi) SEQUENCE DESCRIPTION: SEQ ID NO:11:

Val Leu Gly Gly Gly Ser Ala Leu Leu Arg Ser Ile
1               5                  10

(2) INFORMATION FOR SEQ ID NO:12:

(i) SEQUENCE CHARACTERISTICS:
            (A) LENGTH: 9 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:12:

Val Leu Gly Gly Gly Ser Ala Leu Leu
1               5

(2) INFORMATION FOR SEQ ID NO:13:

(i) SEQUENCE CHARACTERISTICS:
            (A) LENGTH: 20 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:13:

Ile Pro Ala Leu Asp Ser Leu Lys Pro Ala Asn Glu Asp Gln Lys Ile
1               5                  10                  15

Gly Ile Glu Ile
            20

(2) INFORMATION FOR SEQ ID NO:14:

(i) SEQUENCE CHARACTERISTICS:
            (A) LENGTH: 14 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:14:

Val Leu Gly Gly Gly Cys Ala Leu Leu Arg Cys Ile Pro Ala
1               5                  10

(2) INFORMATION FOR SEQ ID NO:15:

(i) SEQUENCE CHARACTERISTICS:
            (A) LENGTH: 5 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:15:

Val Leu Gly Gly Gly
1               5

(2) INFORMATION FOR SEQ ID NO:16:
```

```
      (i) SEQUENCE CHARACTERISTICS:
          (A) LENGTH: 11 amino acids
          (B) TYPE: amino acid
          (C) STRANDEDNESS:
          (D) TOPOLOGY: linear (ii) MOLECULE TYPE: peptide (ix) FEATURE:
          (A) NAME/KEY: Modified-site
          (B) LOCATION: 1
          (D) OTHER INFORMATION: /note= "Xaa = an amino acid
              sequence comprising from 1 to about
              40 amino acids wherein each amino
              acid is independently selected from
              the group consisting of naturally
              occurring amino acids and mimetics"

(ix) FEATURE:
          (A) NAME/KEY: Modified-site
          (B) LOCATION: 11
          (D) OTHER INFORMATION: /note= "Xaa = an amino acid
              sequence comprising from 1 to about
              40 amino acids wherein each amino
              acid is independently selected from
              the group consisting of naturally
              occurring amino acids and mimetics"

(xi) SEQUENCE DESCRIPTION: SEQ ID NO:16:

Xaa Ser Ala Leu Leu Arg Ser Ile Pro Ala Xaa
1               5                   10

(2) INFORMATION FOR SEQ ID NO:17:

(i) SEQUENCE CHARACTERISTICS:
          (A) LENGTH: 4 amino acids
          (B) TYPE: amino acid
          (C) STRANDEDNESS:
          (D) TOPOLOGY: linear (ii) MOLECULE TYPE: peptide (xi) SEQUENCE DESCRIPTION: SEQ ID NO:17:

Val Leu Gly Gly
1

(2) INFORMATION FOR SEQ ID NO:18:

(i) SEQUENCE CHARACTERISTICS:
          (A) LENGTH: 5 amino acids
          (B) TYPE: amino acid
          (C) STRANDEDNESS:
          (D) TOPOLOGY: linear (ii) MOLECULE TYPE: peptide (xi) SEQUENCE DESCRIPTION: SEQ ID NO:18:

Val Leu Gly Gly Val
1               5

(2) INFORMATION FOR SEQ ID NO:19:

(i) SEQUENCE CHARACTERISTICS:
          (A) LENGTH: 5 amino acids
          (B) TYPE: amino acid
          (C) STRANDEDNESS:
          (D) TOPOLOGY: linear (ii) MOLECULE TYPE: peptide (xi) SEQUENCE DESCRIPTION: SEQ ID NO:19:

Gly Val Leu Gly Gly
```

-continued

```
1               5

(2) INFORMATION FOR SEQ ID NO:20:

(i) SEQUENCE CHARACTERISTICS:
        (A) LENGTH: 10 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:20:

Val Glu Glu Gly Ile Val Leu Gly Gly Gly
1               5                   10

(2) INFORMATION FOR SEQ ID NO:21:

(i) SEQUENCE CHARACTERISTICS:
        (A) LENGTH: 4 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:21:

Leu Gly Gly Gly
```

NEUROTROPHIC PEPTIDES OF ACTIVITY DEPENDENT NEUROTROPHIC FACTOR

This application is a continuation-in-part of Ser. No. 07/871,973, filed Apr. 22, 1992 now U.S. Pat. No. 5,767, 240, which is a continuation-in-part of Ser. No. 07/688,087, filed Apr. 22, 1991, now abandoned. The teachings of these two patent application are hereby incorporated in their entirety by reference for all purposes.

FIELD OF THE INVENTION

The present invention relates generally to Activity Dependent Neurotrophic Factor (ADNF). More particularly, the present invention relates to a family of polypeptides derived from ADNF that exhibit neuroprotective/neurotrophic action on neurons originating in the central nervous system and to uses thereof for the treatment of neurological deficiencies and for the prevention of cell death associated with (1) gp120, the envelope protein from HV; (2) N-methyl-D-aspartic acid (excito-toxicity); (3) tetrodotoxin (blockage of electrical activity); and (4) beta-amyloid peptide, a substance related to neuronal degeneration in Alzheimer's disease.

BACKGROUND OF TH INVENTION

Neuronal cell death is characteristic of most developing neural systems in vertebrates. The extent (30–80%) of neuronal death that occurs during development indicates that the regulation of this process is of fundamental importance to the determination of nervous system structure. Although a great deal of descriptive data has been reported concerning the magnitude and ubiquity of this neuronal cell loss, little is known of the mechanism that regulates this process during development. It is clear, however, that electrical activity plays an important role in determining neuronal survival during this regressive phase of development. It has been found, for example, blockage of electrical activity with α-bungarotoxin attenuates the naturally occurring cell death in spinal motoneurons (Pittman and Oppenheim, *Nature* (Lond.) 271, 364–366 (1987)) and in trochlear nucleic in vivo (Creazzo and Sohal, *Exp. Neurol.* 66, 135–145 (1979)).

Studies with cultured spinal cord-dorsal root ganglion (SC-DRG) neurons have shown that during development in vivo, neuronal cell death also occurs in a predictable and activity-dependent manner (Brenneman, et al., *Peptides* 6, 35–39 (1985)). Analysis of the effects of activity blockage on neuronal survival in culture has indicated an interaction between conditioning substances and electrical activity. When endogenous conditioning substances were removed before electrical blockade, neuronal cell death was accelerated (Brenneman, et al., *Dev. Brain Res.* 9, 13–27 (1983)). In contrast, when conditioning substances from SC-DRG cultures were supplied during blockage of electrical activity, neuronal cell death was prevented (Brenneman, et al., *Dev. Brain Res.* 15, 211–217 (1984)).

Further studies have indicated that part of the molecular basis of this activity-dependence is the action of vasoactive intestinal peptide (VIP), a neuropeptide which is released during electrical activity (Brenneman, D. E. and Eiden, L. E., *Proc. Natl. Acad. Sci. U.S.A.* 83, 1159–1162 (1986); and Brenneman, et al., *Peptides* 6, 35–39 (1985)). Moreover, studies have indicated that VIP increases the survival of activity-dependent spinal cord neurons by releasing protein growth factors from non-neuronal spinal cord cells (Brenneman, et al., *J. Cell Biology*, 104, 1603–1610 (1987)). More specifically, it has been determined that VIP interacts with its receptors on glial cells (Gozes, et al., *Soc. Neurosci. Abs.* 15, 216 (1989)) to induce the secretion of neuronal survival factor(s) (Brenneman, et al., *J. Neurosci. Res.* 25, 38&394 (1990); and Gozes, I. and Brenneman, D. E., *Molecular Neurobiology*, 3, 201–236 (1989)).

Among the growth factors released from non-neuronal spinal cord cells by VIP is Activity Dependent Neurotrophic Factor (ADNF). This glia-derived, VIP-released growth factor has been isolated from conditioned medium of rat cerebral cortical astroglia stimulated by VIP (Gozes, 1. & Brenneman, D. E., *Molecular Neurobiology* 3, 1–36 (1989); and Brenneman, D. B. & Eiden, L. E., *Proc. Natl. Acad Sci. U.S.A.* 83, 1159–1162 (1986)). Sequential chromatographic separations by ion exchange, gel permeation and hydrophobic interaction have been utilized to obtain about a 1650-fold purification of a single, 14,000 Dalton protein (apparent pI: 8.3±0.25) that increases survival (EC50, 0.075 pg/ml) of electrically blocked spinal cord neurons and, accordingly, this glia-derived, VIP-released growth factor has been named: Activity Dependent Neurotrophic Factor. ADNF has been shown to protect neuronal cells against death. More particularly, ADNF has been shown to increase the growth and survival of developing spinal cord neurons, hippocampal neurons and cerebral cortical neurons. In addition, ADNF has been found to protect neuronal cell viability by preventing neuronal cell death produced by the external envelope protein of the HV virus.

Although ADNF effectively protects against neuronal cell death, it would be advantageous to have polypeptides which are shorter than the full length amino acid sequence of ADNF, but which exhibit the same neuroprotective/neurotrophic action of the intact ADNF growth factor. Quite surprisingly, the present invention provides such polypeptides.

SUMMARY OF TE INVENTION

An active site for Activity Dependent Neurotrophic Factor (ADNF) has now been discovered. Quite surprisingly, this active site, which is only nine amino acids in length, is more potent than intact ADNF and more effective over a greater range of concentrations (i.e., from 0.01 fm to about 1 pM). This is the first time a polypeptide has been identified which mimics the full biological activity of an intact growth factor. It has further been discovered that other ADNF polypeptides containing this active site also posses the neuroprotective/neurotrophic activity of intact ADNF. As such, the present invention provides a family of ADNF polypeptides, consisting essentially of this ADNF active site, which exhibit the neuroprotective/neurotrophic activity of intact ADNF. These smaller ADNF polypeptides are advantages in that they readily cross the brain barrier. Moreover, due to their length, they do not possess any solubility problems associated with the intact ADNF growth factor.

Quite surprisingly, it has further been discovered that such ADNF polypeptide can be used for the treatment of neurological deficiencies and for the prevention of neuronal cell death. Such ADNF polypeptides can be used, for example, to prevent the death of neuronal cells including, but not limited to, spinal cord neurons, hippocampal neurons, cerebral neurons and cholingeric neurons. More particularly, the ADNF polypeptides of the present invention can be used to prevent cell death associated with (1) gp120, the envelope protein from HIV; (2) N-methyl-D-aspartic acid (excito-toxicity); (3) tetrodotoxin (blockage of electrical activity); and (4) beta-amyloid peptide, a substance related to neuronal degeneration in Alzheimer's disease.

As such, the present invention provides methods for preventing neuronal cell death. More particularly, in one aspect, methods are provided for using the ADNF polypeptides of the present invention to prevent gp120-induced neuronal cell death in a patient infected with HIV. In another aspect, methods are provided for using the ADNF polypeptides of the present invention to prevent neuronal cell death associated with excito-toxicity induced by N-methyl-D-aspartate stimulation. In yet another aspect, methods are provided for using the ADNF polypeptides of the present invention to prevent neuronal cell death induced by the beta-amyloid peptide in a patient afflicted or impaired with Alzheimer's disease. In still another aspect, methods are provided for using the ADNF polypeptides of the present invention to alleviate learning impairment produced by cholingeric blockage in a patient impaired or afflicted with Alzheimer's disease. The ADNF polypeptides of the prevent invention can effectively be used to prevent neuronal cell death associated with a number of other neurological diseases and deficiencies.

Other features, objects and advantages of the invention and its preferred embodiments will become apparent from the detailed description which follows.

BRIEF DESCRIPTION OF THE DRAWINGS

FIG. 3A–C illustrate the biochemical characteristics of purified ADNF.

DEFINITIONS

Figure 1:
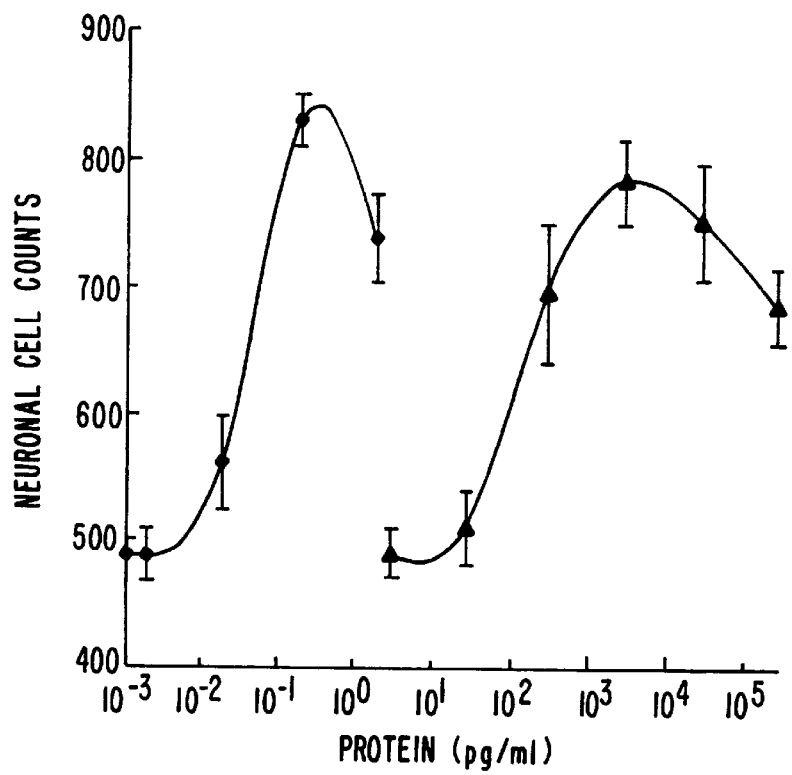
FIG. 1 illustrates the dose response of the survival-promoting activity of ADNF as determined by effects on spinal cord neurons: comparison between conditioned medium and purified ADNF.

"Peptides," "polypeptides" and "oligopeptides" are chains of amino acids (typically L-amino acids) whose a carbons are linked through peptide bonds formed by a condensation reaction between the carboxyl group of the a carbon of one amino acid and the amino group of the a carbon of another amino acid. The terminal amino acid at one end of the chain (i.e., the amino terminal) has a free amino group, while the terminal amino acid at the other end of the chain (i.e., the carboxy terminal) has a free carboxyl group. As such, the term "amino terminus" (abbreviated N-terminus) refers to the free α-amino group on the amino acid at the amino terminal of the peptide, or to the α-amino group (imino group when participating in a peptide bond) of an amino acid at any other location within the peptide. Similarly, the term "carboxy terminus" (abbreviated C-terminus) refers to the free carboxyl group on the amino acid at the carboxy terminus of a peptide, or to the carboxyl group of an amino acid at any other location within the peptide.

Typically, the amino acids making up a polypeptide are numbered in order, starting at the amino terminal and increasing in the direction of the carboxy terminal of the polypeptide. Thus, when one amino acid is said to "follow" another, that amino acid is positioned closer to the carboxy terminal of the polypeptide than the "preceding" amino acid.

The term "residue" is used herein to refer to an amino acid or an amino acid mimetic that is incorporated into a polypeptide by an amide bond or an amide bond mimetic. As such, the amino acid may be a naturally occurring amino acid or, unless otherwise limited, may encompass known analogs of natural amino acids that function in a manner similar to the naturally occurring amino acids (ie., amino acid mimetics). Moreover, an amide bond mimetic includes peptide backbone modifications well known to those skilled in the art.

The term "biologically active" refers to a peptide sequence that will interact with naturally occurring biological molecules to either activate or inhibit the function of those molecules in vitro or in vivo. The term "biologically active" is most commonly used herein to refer to Activity Dependent Neurotrophic Factor polypeptides that exhibit neuroprotective/neurotrophic action on neurons originating in the central nervous system both in vitro or in vivo.

The phrase "consisting essentially of" is used herein to exclude any elements that would substantially alter the essential properties of the ADNF polypeptides or polypeptide antagonists to which the phrase refers. Thus, the description of a polypeptide "consisting essentially of . . . " excludes any amino acid substitutions, additions, or deletions that would substantially alter the biological activity of that polypeptide.

The term "contacting" is used herein interchangeably with the following: combined with, added to, mixed with, passed over, incubated with, flowed over, etc. Moreover, the ADNF polypeptides of the present invention can be "administered" by any conventional method such as, for example, parenteral, oral, topical, and inhalation routes. In presently preferred embodiments, parenteral and nasal inhalation routes are employed.

"An amount sufficient" or "an effective amount" is that amount of a given ADNF polypeptide which exhibits the neuroprotective/neurotrophic activity of interest or, which provides either a subjective relief of a symptom(s) or an objectively identifiable improvement as noted by the clinician or other qualified observer. The dosing range varies with the ADNF polypeptide used, the route of administration and the potency of the particular ADNF polypeptide.

The term "specifically bind(s)" refers to the binding of an ADNF polypeptide to a particular molecule and to no other molecule to which the polypeptide is normally exposed to during the course of its activity.

The amino acids referred to herein are described by shorthand designations as follows:

TABLE I

Amino Acid Nomenclature

| Name | 3-letter | 1 letter |
|---|---|---|
| Alanine | Ala | A |
| Arginine | Arg | R |
| Asparagine | Asn | N |
| Aspartic Acid | Asp | D |
| Cysteine | Cys | C |
| Glutamic Acid | Glu | E |
| Glutamine | Gln | Q |
| Glycine | Gly | G |
| Histidine | His | H |
| Homoserine | Hse | — |
| Isoleucine | Ile | I |
| Leucine | Leu | L |
| Lysine | Lys | K |
| Methionine | Met | M |
| Methionine sulfoxide | Met (O) | — |
| Methionine methylsulfonium | Met (S-Me) | — |
| Norleucine | Nle | — |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

DETAILED DESCRIPTION OF THE INVENTION AND PREFERRED EMBODIMENTS

A. Isolation, Purification And Characterization Of ADNF

The search for the glia-derived, VIP-released Activity Dependent Neurotrophic Factor was based on two previous observations: 1) that glial conditioned medium prevented neuronal cell death in electrically blocked spinal cord test cultures (Brenneman, D. E., et al., *J. Cell Biology,* 104, 1603–1610 (1987)); and 2) that neuron-derived vasoactive intestinal peptide (VIP) increased the release of survival-promoting activity from astroglia (Brenneman, D. E., et al., *J. Neurosci. Res.,* 25, 386–394 (1990)). Secreted proteins (>3,500 Daltons, which excluded VIP) were collected from astroglial cultures treated with 0.1 nM VIP for three hours (FIG. 1). The secreted proteins exhibited distinct electrophoretic patterns which were clearly distinguished from total cellular proteins as well as from proteins secreted from astroglial cells which were not stimulated by VIP (Brenneman, D. E., et al., supra (1990); Brenneman, D. E., Soc. for *Neurosci. Absts.,* 26, 146 (1989)). Survival-promoting activity was tested on neurons from dissociated spinal cord cultures, a well characterized system in which 50% of the neurons die within a critical period of development (Brenneman, D. E., et al., *J. Pharmacol. Exp. Therap.,* 233, 402–408 (1985)). The test cultures (Brenneman, D. E., et al., *Dev. Brain Res.,* 15, 211–217 (1984)) were co-treated with 1 $\mu$M tetrodotoxin to block electrical activity, thereby inhibiting the synthesis and release of VIP (Agoston, D. V., et al., *Mol. Brain Res.,* 10, 235–240 (1991); Brenneman, D. E., et al., *Peptides* 6(2), 35–39 (1985)). The factor responsible for survival activity in the conditioned medium, i.e., ADNF, was trypsin-sensitive and heat-inactivated. FIG. 1 compares the potency of unfractionated conditioned medium (triangles, EC50: 125 pg/ml) to that of purified Activity Dependent Neurotrophic Factor (circles, EC50: 0.075 pg/ml), indicating a 1650-fold purification (see, infra).

Figure 2A:
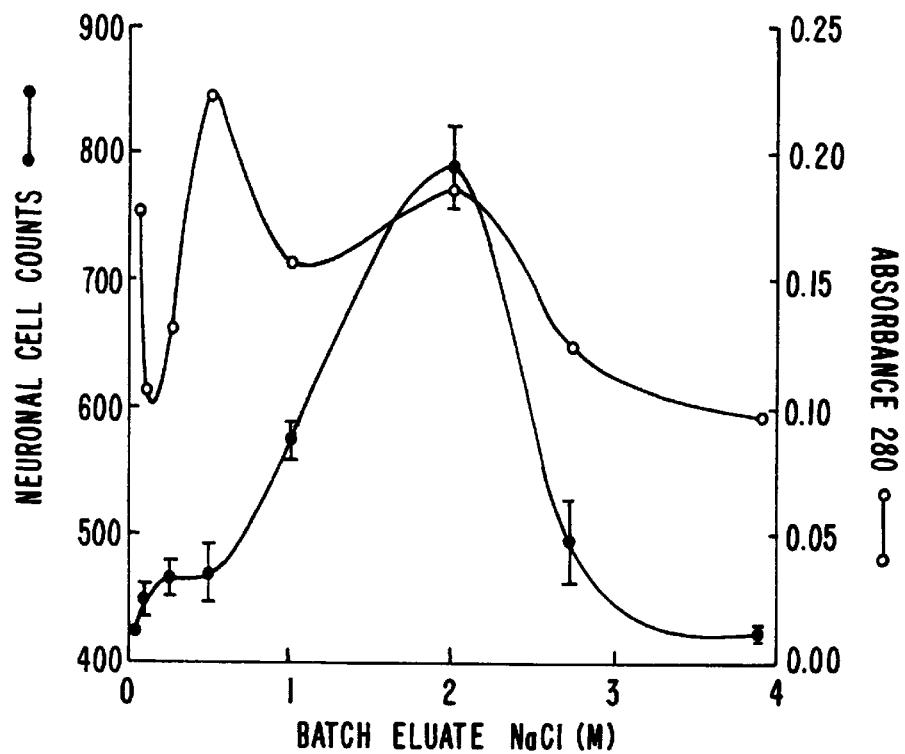
FIG. 2A–C illustrate the purification steps of ADNF as determined by effects on spinal cord neurons.
Figure 2B:
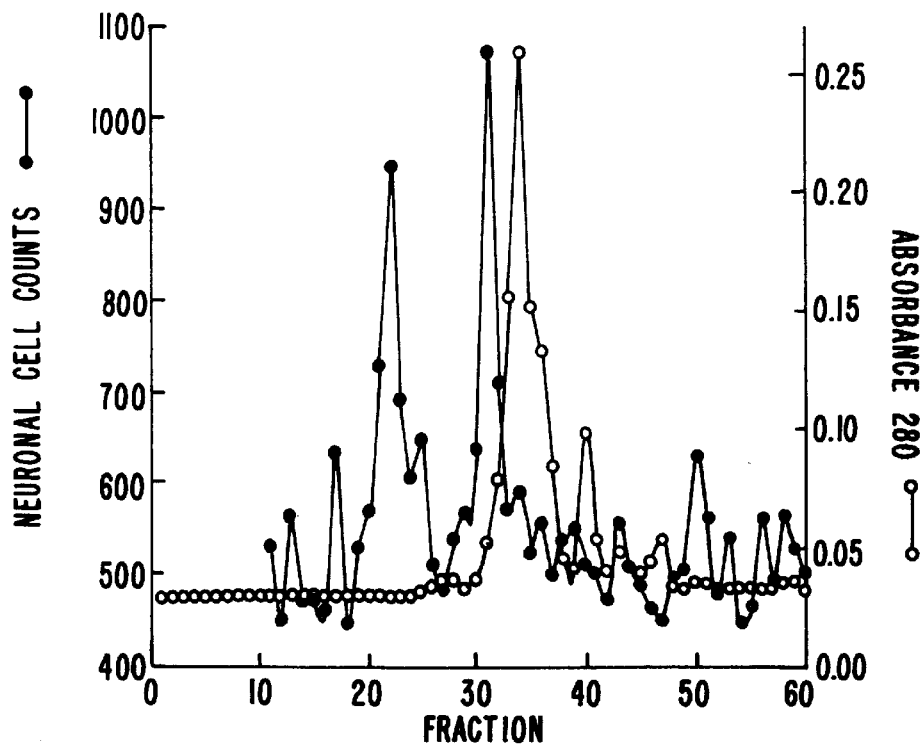
Figure 2C:
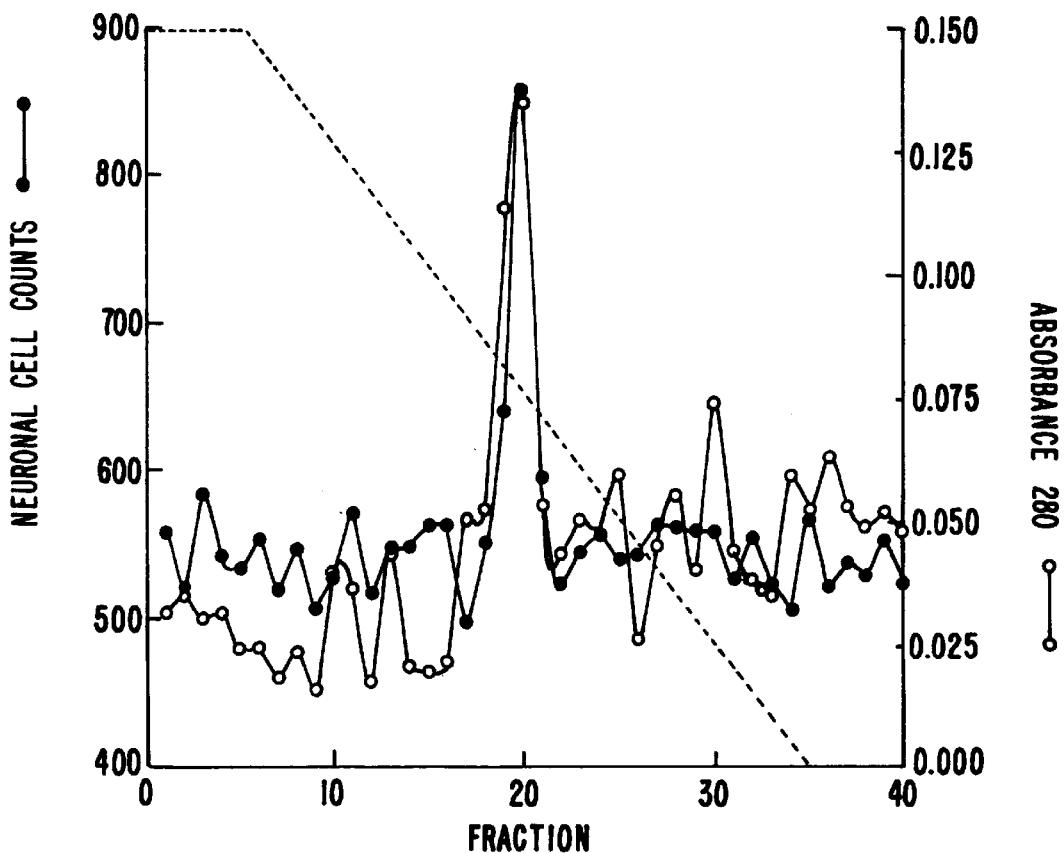

The initial protein purification step by DEAE-Sephacel ion exchange chromatography yielded maximal biological activity in the fraction eluting with 2M NaCl (FIG. 2A). A 10-fold purification of the survival-promoting substance from the unfractionated conditioned medium was observed after anion exchange (See, Table II, infra). As shown in FIG. 2B, the 2M NaCl DEAE-Sephacel eluate was further purified by gel filtration (Superose 12) using fast protein liquid chromatography (FPLC). Two peaks of survival-promoting activity were discovered, one with an apparent molecular weight of 150,000 Daltons and the other with an estimated molecular weight of 16,000 Daltons. The lower molecular weight fraction from the gel filtration column was purified further using hydrophobic interaction chromatography. FIG. 2C shows that the factor responsible for neuronal survival activity was confined to a single peak that eluted in the middle of the desalting gradient. A summary of the purification scheme is given in Table II, infra. The isolated protein was subjected to isoelectric focusing using the MinipHor™ apparatus. Eluted fractions were subjected to pH as well as biological activity assays, revealing a single peak of survival-promoting activity eluting at pH 8.1 FIG. 3A). Isoelectric focusing by electrophoresis on polyacrylamide gels confirmed a single protein band with a pI of 8.3±0.25.

To substantiate the purity of ADNF obtained by the purification scheme outlined in Table II, infra, reverse phase high pressure liquid chromatography (HPLC) and SDS polyacrylamide gel electrophoresis were used. The HPLC analysis indicated a single major peak eluting with a gradient of acetonitrile (FIG. 3B). The material recovered from the HPLC was subjected subsequently to SDS polyacrylamide gel electrophoresis, and was shown to be 99% pure, displaying a molecular weight of about 14,000 Daltons FIG. 3C). The protein band eluted from this SDS gel retained a similar specific activity in the survival assay to that observed after hydrophobic interaction chromatography (Table II, infra).

Figure 4:
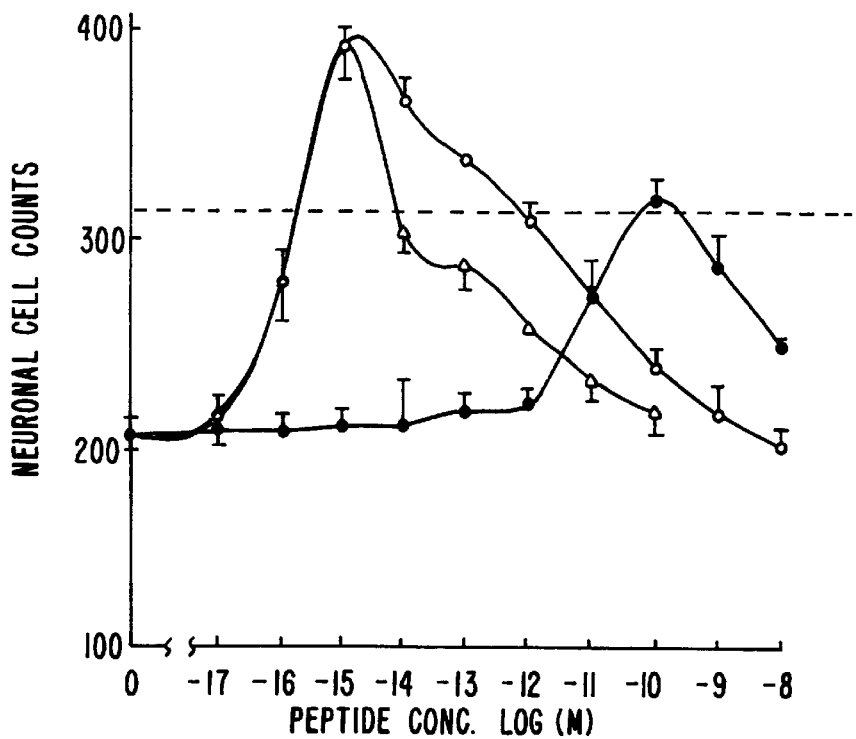
FIG. 4 illustrates a comparison of neuronal survival-promoting activity of intact ADNF, ADNF-14 and a hsp60 peptide in tetrodotoxin-treated cerebral cortical cultures.

To establish the relevance of ADNF in a neuronal system homologous to the rat cortical astrocyte cultures, purified ADNF was tested in mixed neuronal/glial cultures obtained from term rat cerebral cortex (Hill, J. M., et al., *Brain Res.* 603, 222–233 (1993)). As shown in FIG. 4, the purified ADNF exhibited extraordinary potency (EC50: 0.3 fM) in increasing neuronal survival during a five day test period. Cell death associated with tetrodotoxin as well as that which occurred naturally in these cultures was prevented by ADNF treatment. Furthermore, the addition of ADNF in the absence of tetrodotoxin also increased neuronal survival at similar concentrations in cerebral cortical cultures (data not shown). These results indicate a broad spectrum of biological activity for ADNF in that activity was detected in both mouse spinal cord and rat cerebral cortex cultures.

less than the full length amino acid sequence of ADNF, but which exhibit the same neuroprotective/neurotrophic action of the intact ADNF growth factor can now be prepared.

More particularly, based on the sequence analyses after protease digestion of ADNF and the recognized homology to hsp60, ADNF-14, i.e., Val-Leu-Gly-Gly-Gly-Ser-Ala-Leu-Leu-Arg-Ser-Ile-Pro-Ala(SEQ ID NO: 1) , was identified. As shown in FIG. 4, ADNF-14 increases neuronal survival with an EC50 of 0.3 fM, a potency identical to the activity of intact ADNF in this culture system. Moreover, ADNF-14 is active over a wider range of concentrations than that observed for intact ADNF. Importantly, the homologous polypeptide from hsp60, i.e., Val-Leu-Gly-Gly-Gly-Cys-Ala-Leu-Leu-Arg-Cys-Ile-Pro-Ala(SEQ ID NO: 14), was also tested and shown to be 100,000-fold less potent and

TABLE II

Summary of purification of Activity Dependent Neurotrophic Factor.
The conditioned medium (300 ml) was from rat astroglia cultures stimulated with 0.1 nM VIP.

| STEP | PROTEIN ($\mu$g) | UNITS (million) | SPECIFIC ACTIVITY (Units*/ng) | RECOVERY (%) | FOLD PURIFICATION |
|---|---|---|---|---|---|
| 1. Conditioned Medium | 5400 | 43.0 | 8 | 100 | |
| 2. DEAE | 467 | 41.5 | 89 | 96.5 | 11.12 |
| 3. Sizing | 5 | 5.5 | 1100 | 12.8 | 137.5 |
| 4. Hydrophobic Interaction | 0.28 | 3.7 | 13,200 | 8.6 | 1650 |

*A unit was determined by the amount of protein which elicited a half maximal response in the survival assay. Observed decreases in activity after sizing and hydrophobic interaction may be due to the dialysis procedure and the existence of multiple neurotrophic substances (see FIG. 2B).
Yield: 0.005%
Purification: 1650×

Once purified, the fundamental issue was the determination of the amino acid sequence of ADNF. When purified ADNF was analyzed by Edman degradation, N-terminal blockade was observed. ADNF, after HPLC reverse phase chromatography (FIG. 3B), was then digested with V8 protease and the resulting peptides separated by HPLC (as in FIG. 3B). Four overlapping peptides were sequenced, all of which showed sequence homology to rat heat shock protein (hsp) 60 corresponding to positions 448–467 (including the 26 amino acid leader sequences (Venner, T. J., et al., *Nucleic Acid Res.* 18, 5309 (1990; Peralta, D., et al., *Nucleic Acid Res.*, 18, 7162 (1990)). Sizing analysis of the neurotrophic activity present in the conditioned medium gave no indication of survival-promoting activity in the 40–70 kDalton range (See, FIG. 2B). These data suggested that a protein related to hsp60 accounted for the survival-promoting activity and that this protein was secreted by VIP-stimulated astroglia.

B. Neurotrophic Polypeptides of ADNF

Based on the sequence analyses after protease digestion of ADNF and the recognized homology to hsp60, a large number of ADNF polypeptides, which are shorter in length than intact ADNF, were synthesized and tested for neuroprotective activity in tetrodotoxin-treated cerebral cortical cultures. The synthesized peptides were chosen to include regions of observed sequence difference between hsp60 and ADNF, with the rationale being that ADNF would have functions distinct from that of hsp60. From an analysis of such ADNF polypeptides, the molecular identity of an active site for ADNF has now been discovered. Based on this newly discovered active site, ADNF polypeptides which are about 50% less efficacious than both ADNF-14 and intact ADNF (see, FIG. 4). These data indicate that the two amino acid residues that are different between ADNF-14 and the hsp60 polypeptide (i.e., the two serine residues) are critical for the survival-promoting activity for CNS neurons. ADNF-14 is the first demonstration of an ADNF polypeptide which is less than the full length amino acid sequence of ADNF, but which exhibits the same neuroprotective/neurotrophic action of the intact ADNF growth factor. Moreover, this is the first time the molecular identity of an active site for ADNF has been identified, confirming the structure and extraordinary potency of the ADNF molecule.

Figure 5:
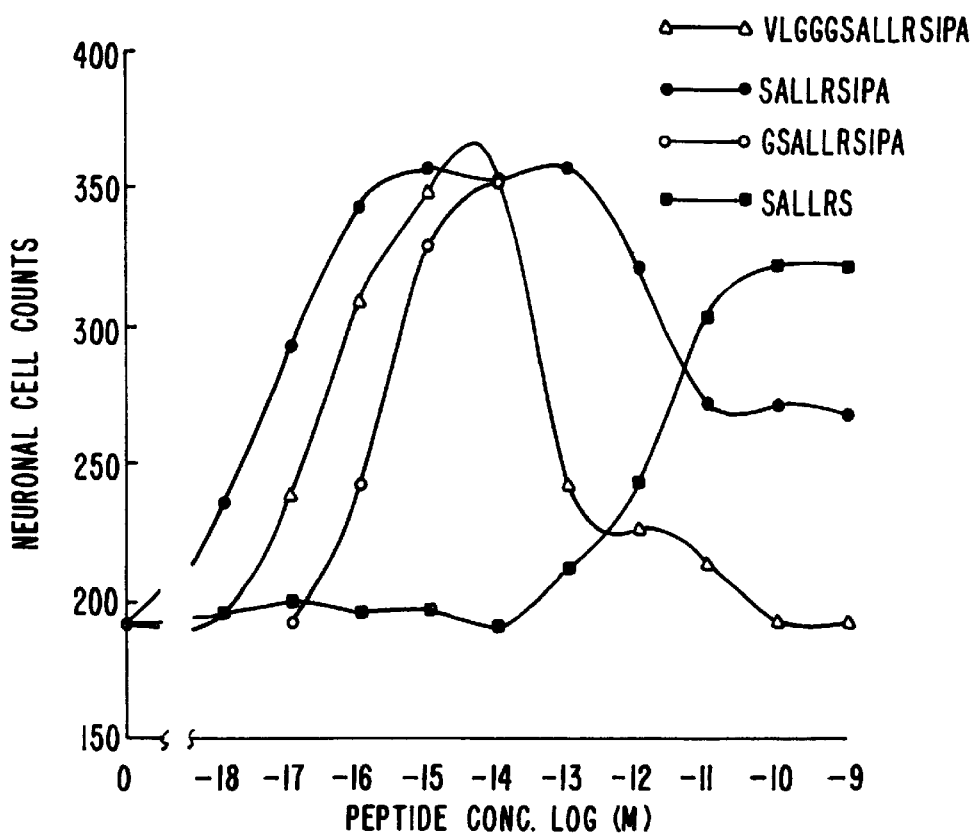
FIG. 5 illustrates the structure-activity relationships of ADNF-related peptides in terms of their ability to increase neuronal survival in TTX-treated cerebral cortical cultures (VLGGGSALLRSIPA (SEQ ID NO: 1); SALLRSIPA (SEQ ID NO:2); GSALLRSIPA (SEQ ID NO:3); and SALLRS (SEQ ID NO:4)).
Figure 6:
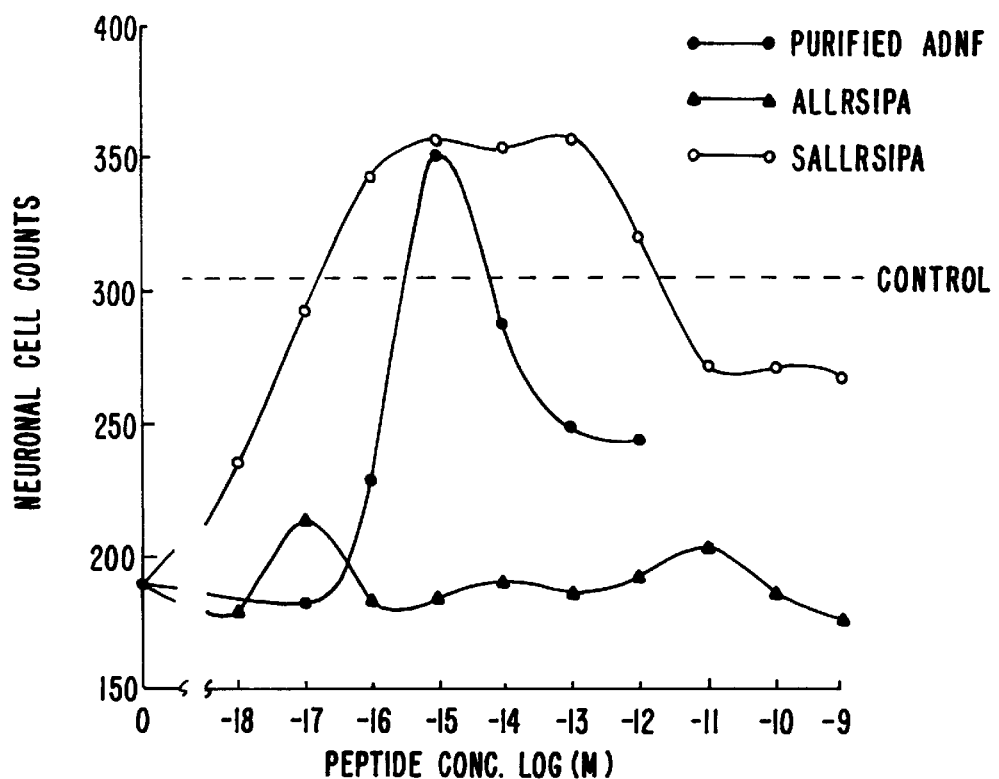
FIG. 6 illustrates a comparison of purified ADNF with ADNF-related peptides in terms of their effect on neuronal survival in TTX-treated cerebral cortical cultures (ALLRSIPA (SEQ ID NO:5); and SALLRSIPA (SEQ ID NO:2)) .

Using ADNF-14 as a model, further additions, deletions, substitutions, etc. were made to ADNF-14 to further define the active site for ADNF. In doing so, ADNF polypeptides which are shorter in length than ADNF-14 were synthesized and tested for neuroprotective activity to determine the smallest ADNF-related polypeptide that exhibits the full efficacy of intact or native ADNF. In doing so, ADNF-9, i.e., Ser-Ala-Leu-Leu-Arg-Ser-Ile-Pro-Ala(SEQ ID NO: 2), was synthesized. As shown in FIGS. 5 and 6, ADNF-9 is more potent than ADNF-14 and more effective over a greater range of concentrations (i.e., from 0.01 fm to about 1 pM). As such, it can be said that the Val-Leu-Gly-Gly-Gly-(SEQ ID NO: 15) portion of ADNF-14 is not essential to the survival-promoting activity of ADNF. Moreover, it has been determined that removal of the Ile-Pro-Ala portion of ADNF-9 results in a 100,000 fold loss in potency. In addition, the importance of the N-terminal serine in ADNF-9 is evident in that the polypeptide Ala-Leu-Leu-Arg-Ser-Ile-Pro-Ala(SEQ ID NO: 5) is devoid of significant activity (see, FIG. 6). These data indicate the importance of the Ile-Pro-Ala portion as well as the two serine residues in the survival-promoting activity of ADNF-9 and, in turn, intact ADNF.

Figure 7:
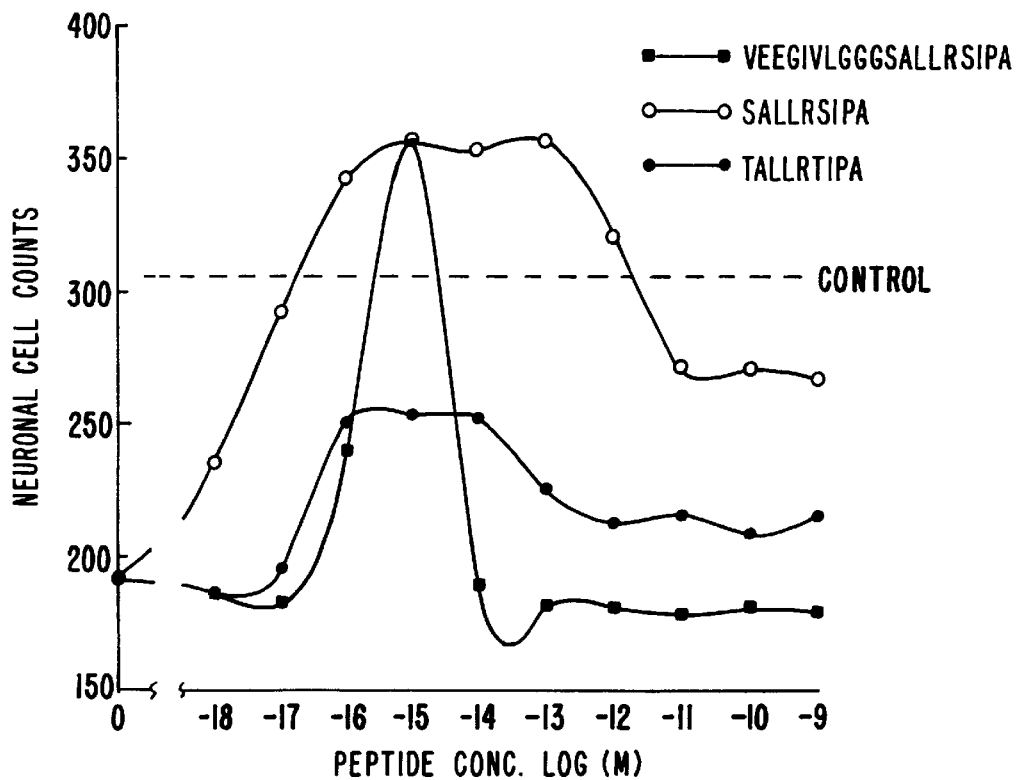
FIG. 7 illustrates the effect of conservative substitutions and peptide elongation on survival-promoting activity of ADNF-Peptide, i.e., SALLRSIPA (SEQ ID NO:2); (VEEGIVLGGGSALLRSIPA (SEQ ID NO:6); SALLR-SIPA (SEQ ID NO:2); and TALLRTIPA (SEQ ID NO:7).
Figure 8:
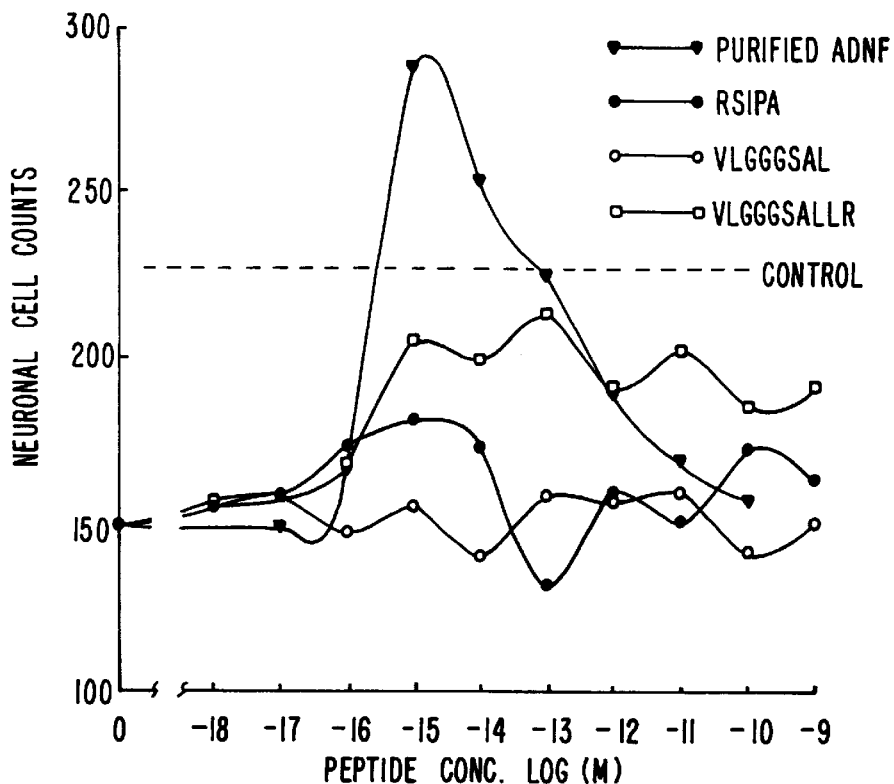
FIG. 8 illustrates the structure-activity relationships of ADNF-related peptides in terms of their ability to increase neuronal survival in TTX-treated cerebral cortical cultures (RSIPA (SEQ ID NO:8); VLGGGSAL (SEQ ID NO:9); and VLGGGSALLR (SEQ ID NO:10).
Figure 9:
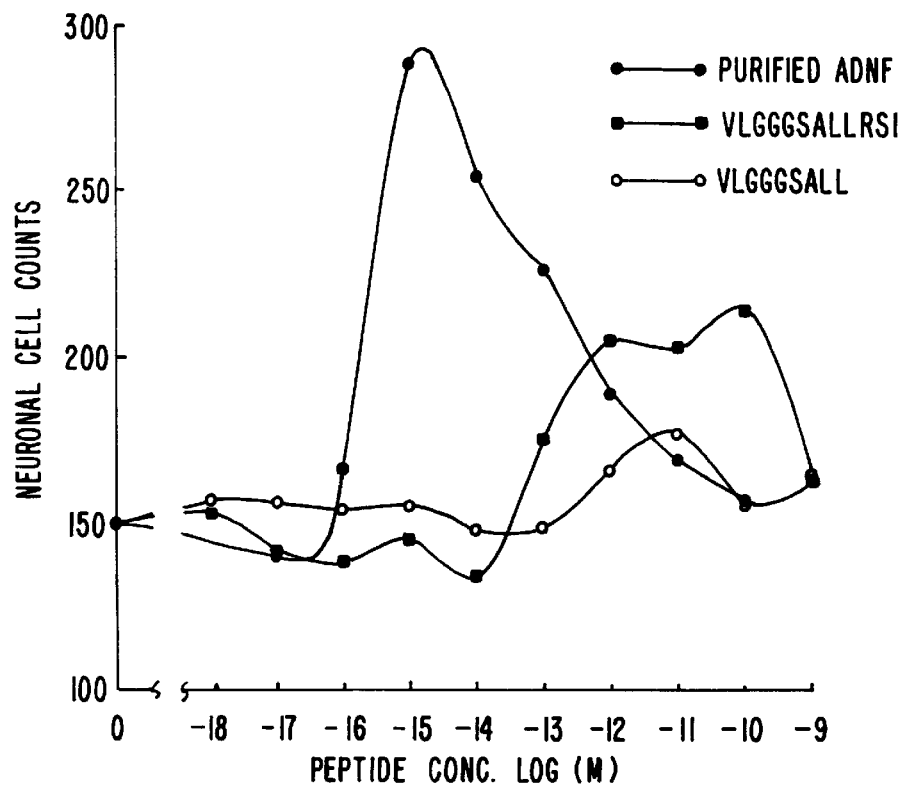
FIG. 9 illustrates the structure-activity relationships of ADNF-related peptides in terms of their ability to increase neuronal survival in TTX-treated cerebral cortical cultures (VLGGGSALLRSI (SEQ ID NO:11); and VLGGGSALL (SEQ ID NO: 12).

To determine the smallest ADNF polypeptide which exhibits the same neuroprotective/neurotrophic action of the intact ADNF growth factor, further additions and deletions were made to ADNF-9 and ADNF-14. In doing so, it was found that Arg-Ser-Ile-Pro-Ala(SEQ ID NO: 8), Val-Leu-Gly-Gly-Gly-Ser-Ala-Leu(SEQ ID NO: 9), Val-Leu-Gly-Gly-Gly-Ser-Ala-Leu-Leu-Arg(SEQ ID NO: 10) and Val-Leu-Gly-Gly-Gly-Ser-Ala-Leu-Leu(SEQ ID NO: 12) all exhibited reduced survival-promoting activity or, alternatively, no survival-promoting activity (see, FIGS. 8 and 9). These data indicate that Ser-Ala-leu-Leu-Arg-Ser-Ile-Pro-Ala(SEQ ID NO: 2), i.e., ADNF-9, is the smallest ADNF polypeptide which exhibits the same neuroprotective/neurotrophic action of the intact ADNF growth factor. Moreover, these data also confirm the importance of the Ile-Pro-Ala portion as well as the two serine residues in the survival-promoting activity of ADNF-9. It should be noted that additional amino acids can be added to ADNF-9 without loss of activity. For example, additional amino acids related to hsp60 can be added to ADNF-9 without loss of activity (see, FIG. 7). Moreover, conservative substitutions can be made to ADNF-9, albeit with some loss of biological activity. For example, conservative substitution of threonine for serine in Ser-Ala-Leu-Leu-Arg-Ser-Ile-Pro-Ala(SEQ ID NO: 2) results in another biologically active ADNF polypeptide, i.e., Thr-Ala-Leu-Leu-Arg-Thr-Ile-Pro-Ala(SEQ ID NO: 7) (see, FIG. 7).

From the foregoing, it is readily apparent that ADNF-9, i.e., Ser-Ala-Leu-Leu-Arg-Ser-Ile-Pro-Ala, (SEQ ID NO: 2) is an active site for ADNF. ADNF-9 can match the efficacy of purified, intact ADNF growth factor and, in addition, it exhibits this efficacy over four orders of magnitude, i.e., from $10^{-16}$ to $10^{-13}$ M. ADNF-9 is the smallest ADNF-related polypeptide to exhibit the full efficacy of ADNF and, thus, in order for ADNF polypeptides to exhibit substantially the same neuroprotective/neurotrophic action of the intact ADNF growth factor, they must contain this newly discovered active site. It should be noted, however, that conservative substitutions (e.g., the substitution of threonine for serine) can be made to this active site with some loss of biological activity. Moreover, additional amino acids can be added to both the N-terminus and C-terminus of ADNF-9 to produce other ADNF polypeptides that provide the same protective action as the intact growth factor. Thus, ADNF polypeptides containing the active site Ser-Ala-Leu-Leu-Arg-Ser-Ile-Pro-Ala, (SEQ ID NO: 2) either alone or in combination with other amino acids, will exhibit substantially the same neuroprotective/neurotrophic activity of the intact ADNF growth factor.

As such, in one aspect of the present invention, an Activity Dependent Neurotrophic Factor (ADNF) polypeptide is provided, the ADNF polypeptide consisting essentially of the following amino acid sequence:

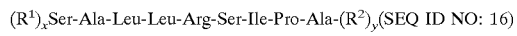

(R$^1$)$_x$Ser-Ala-Leu-Leu-Arg-Ser-Ile-Pro-Ala-(R$^2$)$_y$(SEQ ID NO: 16)

In the above formula, R$^1$ is an amino acid sequence comprising from 1 to about 40 amino acids wherein each amino acid is independently selected from the group consisting of naturally occurring amino acids and amino acid mimetics. The term "independently selected" is used herein to indicate that the amino acids making up the amino acid sequence R$^1$ may be identical or different (e.g., all of the amino acids in the amino acid sequence may be threonine, etc.). Moreover, as previously explained, the amino acids making up the amino acid sequence R$^1$ may be either naturally occurring amino acids, or known analogs of natural amino acids that functions in a manner similar to the naturally occurring amino acids (i.e., amino acid mimetics). Suitable amino acids that can be used to form the amino acid sequence R$^1$ include, but are not limited to, those listed in Table I, supra.

As with R$^1$, R$^2$, in the above formula, is an amino acid sequence comprising from 1 to about 40 amino acids wherein each amino acid is independently selected from the group consisting of naturally occurring amino acids and amino acid mimetics. Moreover, as with R$^1$, the amino acids making up the amino acid sequence R$^2$ may be identical or different, and may be either naturally occurring amino acids, or known analogs of natural amino acids that functions in a manner similar to the naturally occurring amino acids (i.e., amino acid mimetics). Suitable amino acids that can be used to form R$^2$ include, but are not limited to, those listed in Table I, supra.

Within the above formula, x and y are independently selected and are equal to zero or one. The term independently selected is used herein to indicate that x and y may identical or different. For example, x and y may both be zero or, alternatively, x and y may both be one. In addition, x may be zero and y may be one or, alternatively, x may be one and y may be zero. Moreover, if x and y are both one, the amino acid sequences R$^1$ and R$^2$ may be the same or different. As such, the amino acid sequences R$^1$ and R$^2$ are independently selected. If R$^1$ and R$^2$ are the same, they are identical in terms of both chain length and amino acid composition. For example, both R$^1$ and R$^2$ may be Val-Leu-Gly-Gly-Gly. (SEQ ID NO: 15) If R$^1$ and R$^2$ are different, they can differ from one another in terms of chain length and/or amino acid composition and/or order of amino acids in the amino acids sequences. For example, R$^1$ may be Val-Leu-Gly-Gly-Gly (SEQ ID NO: 15), whereas R$^2$ may be Val-Leu-Gly-Gly (SEQ ID NO: 17). Alternatively, R$^1$ may be Val-Leu-Gly-Gly-Gly, whereas R$^2$ may be Val-Leu-Gly-Gly-Val(SEQ ID NO: 18). Alternatively, R$^1$ may be Val-Leu-Gly-Gly-Gly (SEQ ID NO: 19), whereas R$^2$ may be Gly-Val-Leu-Gly-Gly.

Within the scope of the above formula, certain ADNF polypeptides are preferred, namely those in which x and y are both zero (i.e., ADNF-9). Equally preferred are ADNF polypeptides in which x is one; R$^1$ is Val-Leu-Gly-Gly-Gly; and y is zero (i.e., ADNF-14). Also equally preferred are ADNF polypeptides in which x is one; R$^1$ is Val-Glu-Glu-Gly-Ile-Val-Leu-Gly-Gly-Gly(SEQ ID NO: 20); and y is zero. Additional amino acids can be added to both the N-terminus and the C-terminus of the newly discovered active site without loss of biological activity as evidenced by the fact that the intact ADNF growth fact exhibits extraordinary biological activity. It should be noted, however, that in all embodiments of the present invention, R$^1$, R$^2$, x and y are selected such that the ADNF polypeptides of the present invention have other than the full length amino acid sequence of intact Activity Dependent Neurotrophic Factor.

In addition, it will be readily apparent to those of ordinary skill in the art that the ADNF polypeptides of the present invention may be subject to various changes, such as insertions, deletions, and substitutions, either conservative or non-conservative, where such changes might provide for certain advantages in their use, i.e., to increase biological activity. By conservative substitutions is meant replacing an amino acid residue with another which is biologically and/or chemically similar, e.g., one hydrophobic residue for another, or one polar residue for another. The substitutions include combinations such as, for example, Gly, Ala; Val, Ile, Leu; Asp, Glu; Asn, Gln; Ser, Thr; Lys, Arg; and Phe, Tyr. In fact, as previously explained, it has been determined that conservative substitutions of threonine for serine in Ser-Ala-Leu-Leu-Arg-Ser-Ile-Pro-Ala(SEQ ID NO: 2) result in a biologically active ADNF polypeptide, i.e., Thr-Ala-Leu-Leu-Arg-Thr-Ile-Pro-Ala(SEQ ID NO: 7) (See, FIG. 7). Other residues which can be modified without loosing the biological activity of the ADNF polypeptides can be identified by single amino acid substitutions, deletions, or insertions using conventional techniques known to those of ordinary skill in the art, this is especially true of the ADNF polypeptides of the present invention being that they are relatively short in length. In addition, the contributions made by the side chains of the residues can be probed via a systematic scan with a specified amino acid (e.g., Ala).

Moreover, it will be readily apparent to those of ordinary skill in the art that the ADNF polypeptides of the present invention can readily be screened for neuroprotective/neurotrophic activity by employing the following CNS assay. Cerebral cortical cell cultures are prepared using the techniques described by I. Forsythe and G. Westbrook, *J. Physiol. Lond.* 396:515 (1988) with the following modifications. Cerebral cortex are used instead of hippocampus, and newborn rats are used instead of E16 mice. After nine days growth in vitro, the cultures are given a complete change of medium and treated with the ADNF polypeptide of interest (dissolved in phosphate buffered saline or ethanol) for an additional five days. To terminate, the cells are fixed for immunocytochemistry and neurons identified with antibodies against NSE (i.e., neuron specific enolase, a neuronal specific marker). Cell counts are performed on 30 fields, with total area of about 15 mm². Neurons are counted without knowledge of treatment. Control counts not treated with any drugs should run for purposes of comparison.

Using this assay, one of ordinary skill in the art can readily prepare a large number of ADNF polypeptides in accordance with the foregoing teachings and, in turn, screen them using the foregoing assay to find ADNF polypeptides, in addition to those set forth herein, which possess the neuroprotective/neurotrophic activity of the intact ADNF growth factor. For instance, using ADNF-9 as a starting point, one can systematically add, for example, GLY-, Gly-Gly-, Gly-Gly-Gly-, Leu-Gly-Gly-Gly-(SEQ ID NO: 21), Val-Leu-Gly-Gly-Gly (SEQ ID NO: 15) to the N-terminus of ADNF-9 and, in turn, screen each of these ADNF polypeptides in the foregoing assay to determine whether they possess neuroprotective/neurotrophic activity. In doing so, it will be found that additional amino acids can be added to both the N-terminus and the C-terminus of the newly discovered active site, i.e., Ser-Ala-Leu-Leu-Arg-Ser-Ile-Pro-Ala, (SEQ ID NO: 2) without loss of biological activity as evidenced by the fact that the intact ADNF growth fact exhibits extraordinary biological activity.

Since the ADNF polypeptides of the present invention are relatively short in length, they can be prepared using any of a number of chemical peptide synthesis techniques well known to those of ordinary skill in the art including both solution methods and solid phase methods, with solid phase synthesis being presently preferred.

In particular, solid phase synthesis in which the C-terminal amino acid of the peptide sequence is attached to an insoluble support followed by sequential addition of the remaining amino acids in the sequence is the preferred method for preparing the ADNF polypeptides of the present invention. Techniques for solid phase synthesis are described by Barany and Merrifield, *Solid-Phase Peptide Synthesis, in The Peptides: Analysis, Synthesis, Biology* (Gross and Meienhofer (eds.), Academic Press, N.Y., vol. 2, pp. 3–284 (1980)); Merrifield, et al., *J. Am. Chem. Soc.* 85, 2149–2156 (1963); and Stewart, et al., *Solid Phase Peptide Synthesis* (2nd ed., Pierce Chem. Co., Rockford, Ill. (1984)), the teachings of which are hereby incorporated by reference.

Solid phase synthesis is started from the carboxy-terminal end (i.e., the C-terminus) of the peptide by coupling a protected amino acid via its carboxyl group to a suitable solid support. The solid support used is not a critical feature of the present invention provided that it is capable of binding to the carboxyl group while remaining substantially inert to the reagents utilized in the peptide synthesis procedure. For example, a starting material can be prepared by attaching an amino-protected amino acid via a benzyl ester linkage to a chloromethylated resin or a hydroxymethyl resin or via an amide bond to a benzhydrylamine (BHA) resin or p-methylbenzhydrylamine (MBHA) resin. Materials suitable for us as solid supports are well known to those of skill in the art and include, but are not limited to, the following: halomethyl resins, such as chloromethyl resin or bromomethyl resin; hydroxymethyl resins; phenol resins, such as 4-(α-[2,4-dimethoxyphenyl]-Fmoc-aminomethyl)phenoxy resin; tert-alkyloxycarbonyl-hydrazidated resins, and the like. Such resins are commercially available and their methods of preparation are known by those of ordinary skill in the art.

The acid form of the peptides of the present invention may be prepared by the solid phase peptide synthesis procedure using a benzyl ester resin as a solid support. The corresponding amides may be produced by using benzhydrylamine or methylbenz-hydrylamine resin as the solid support. Those skilled in the art will recognize that when the BHA or MBHA resin is used, treatment with anhydrous hydrofluoric acid to cleave the polypeptide from the solid support produces a polypeptide having a terminal amide group.

The α-amino group of each amino acid used in the synthesis should be protected during the coupling reaction to prevent side reactions involving the reactive α-amino function. Certain amino acids also contain reactive side-chain functional groups (e.g. sulfhydryl, amino, carboxyl, hydroxyl, etc.) which must also be protected with appropriate protecting groups to prevent chemical reactions from occurring at those sites during the polypeptide synthesis. Protecting groups are well known to those of skill in the art. See, for example, *The Peptides: Analysis, Synthesis, Biology*, Vol. 3: *Protection of Functional Groups in Peptide Synthesis* (Gross and Meienhofer (eds.), Academic Press, N.Y. (1981)), the teachings of which are incorporated herein by reference.

A properly selected α-amino protecting group will render the α-amino function inert during the coupling reaction, will be readily removable after coupling under conditions that will not remove side chain protecting groups, will not alter the structure of the peptide fragment, and will prevent racemization upon activation immediately prior to coupling. Similarly, side-chain protecting groups must be chosen to render the side chain functional group inert during the synthesis, must be stable under the conditions used to remove the a-amino protecting group, and must be removable after completion of the polypeptide synthesis under conditions that will not alter the structure of the polypeptide.

Mustrative examples of protecting groups for an a-amino group include, but are not limited to, the following: aromatic urethane-type groups such as, for example, fluorenylmethyloxycarbonyl (Fmoc), carbobenzoxy (Cbz), and substituted benzyloxycarbonyls including p-chlorobenzyloxycarbonyl, o-chlorobenzyloxycarbonyl, 2,4-dichlorobenzyloxycarbonyl, 2,6-dichlorobenzyloxycarbonyl, etc.; aliphatic urethane-type groups such as, for example, butyloxycarbonyl (Boc), t-amyloxycarbonyl, isopropyloxycarbonyl, 2-(p-biphenylyl)-isopropyloxycarbonyl, allyloxycarbonyl, etc.; and cycloalkyl urethane-type groups such as, for example, cyclopentyloxycarbonyl, cyclohexyloxycarbonyl, cycloheptyloxy-carbonyl, adamantyloxycarbonyl (Adoc), etc. In a presently preferred embodiment, fluorenylmethyloxycarbonyl (Fmoc) is the a-amino protecting group used.

For the side chain amino group present in lysine (Lys), any of the protecting groups described above for the protection of the α-amino group are suitable. Moreover, other suitable protecting groups include, but are not limited to, the following: butyloxycarbonyl (Boc), p-chlorobenzyloxycarbonyl, p-bromobenzyloxycarbonyl, o-chlorobenzyloxycarbonyl, 2,6-dichlorobenzyloxycarbonyl, 2,4-dichlorobenzyl-oxycarbonyl, o-bromobenzyloxycarbonyl, p-nitrobenzyloxycarbonyl, t-butyloxycarbonyl, isopropyloxycarbonyl, t-amyloxycarbonyl, cyclopentyloxycarbonyl, cyclohexyl-oxycarbonyl, cycloheptyloxycarbonyl, adamantyloxycarbonyl, p-toluenesulfonyl, etc. In a presently preferred embodiment, the side chain amino protecting group for Lys is butyloxycarbonyl (Boc).

For protection of the guanidino group of arginine (Arg), examples of suitable protecting groups include, but are not limited to, the following: nitro, tosyl (Tos), carbobenzoxy (Cbz), adamantyloxycarbonyl (Adoc), butyloxycarbonyl (Boc), 4-methoxy-2,3,6-trimethylbenzenesulfonyl (Mtr) and 2,2,5,7,8-pentamethylchloroman-6-sulfonyl (PMC). In a presently preferred embodiment, 4-methoxy-2,3,6-trimethyl-benzenesulfonyl and 2,2,5,7,8-pentamethylchloroman-6sulfonyl are the protecting group used for Arg.

The hydroxyl group on the side chains of serine (Ser), threonine (Thr) or tyrosine (Tyr) can be protected by a $C_1$–$C_4$ alkyl such as, for example, methyl, ethyl and t-butyl, or by a substituted benzyl such as, for example, p-methoxybenzyl, p-nitrobenzyl, p-chlorobenzyl, o-chlorobenzyl and 2,6-dichlorobenzyl. The preferred aliphatic hydroxyl protecting group for Ser, Thr and Tyr is t-butyl.

The carboxyl group of aspartic acid (Asp) may be protected by, for example, esterification using groups such as benzyl, t-butyl, cyclohexyl, cyclopentyl, and the like. For Asp, t-butyl is the presently preferred protecting group.

The basic imidazole ring in histidine (His) may be protected by, for example, t-butoxymethyl (Bom), butyloxycarbonyl (Boc) and fluorenylmethyloxycarbonyl (Fmoc). In a preferred embodiment, t-butoxymethyl (Bom) is the protecting group used.

Coupling of the amino acids may be accomplished by a variety of chemistries known to those of skill in the art. Typical approaches involve either the conversion of the amino acid to a derivative that will render the carboxyl group more susceptible to reaction with the free N-terminal amino group of the polypeptide fragment, or use of a suitable coupling agent such as, for example, N,N'-dicyclohexylcarbodimide (DCC) or N,N'-diisopropylcarbodiimide (DIPCDI). Frequently, hydroxybenzotriazole (HOBt) is employed as a catalyst in these coupling reactions. Appropriate synthesis chemistries are disclosed in *The Peptides: Analysis, Structure, Biology*, Vol. 1: *Methods of Peptide Bond Formation* (Gross and Meienhofer (eds.), Academic Press, N.Y. (1979)); and Izumiya, et al., *Synthesis of Peptides* Maruzen Publishing Co., Ltd., (1975)), both of which are incorporated herein by reference.

Generally, synthesis of the polypeptide is commenced by first coupling the C-terminal amino acid, which is protected at the Nα-amino position by a protecting group such as fluorenylmethyloxycarbonyl (Fmoc), to a solid support. Prior to coupling of Fmoc-Asn, the Fmoc residue has to be removed from the polymer. Fmoc-Asn can, for example, be coupled to the 4-(α-[2,4-dimethoxyphenyl]-Fmoc-aminomethyl)phenoxy resin using N,N'-dicyclohexylcarbodiimide (DCC) and hydroxybenzotriazole (HOBt) at about 25° C. for about two hours with stirring. Following the coupling of the Fmoc-protected amino acid to the resin support, the α-amino protecting group is removed using 20% piperidine in DMF at room temperature.

After removal of the α-amino protecting group, the remaining Fmoc-protected amino acids are coupled stepwise in the desired order. Appropriately protected amino acids are commercially available from a number of suppliers (e.g., Nova (Switzerland) or Bachem (California)). As an alternative to the stepwise addition of individual amino acids, appropriately protected peptide fragments consisting of more than one amino acid may also be coupled to the "growing" polypeptide. Selection of an appropriate coupling reagent, as explained above, is well known to those of skill in the art. It should be noted that since the ADNF polypeptides of the present invention are relative short in length, this latter approach (i.e., the segment condensation method) is not the most efficient method of peptide synthesis.

Each protected amino acid or amino acid sequence is introduced into the solid phase reactor in excess and the coupling is carried out in a medium of dimethylformamide (DMF), methylene chloride ($CH_2Cl_2$) or, mixtures thereof. If coupling is incomplete, the coupling reaction may be repeated before deprotection of the Nα-amino group and addition of the next amino acid. Coupling efficiency may be monitored by a number of means well known to those of skill in the art. A preferred method of monitoring coupling efficiency is by the ninhydrin reaction. Polypeptide synthesis reactions may be performed automatically using a number of commercially available peptide synthesizers (e.g., Biosearch 9500, Biosearch, San Raphael, Calif.).

The peptide can be cleaved and the protecting groups removed by stirring the insoluble carrier or solid support in anhydrous, liquid hydrogen fluoride (HF) in the presence of anisole and dimethylsulfide at about 0° C. for about 20 to 90 minutes, preferably 60 minutes; by bubbling hydrogen bromide (HBr) continuously through a 1 mg/10 mL suspension of the resin in trifluoroacetic acid (TFA) for 60 to 360 minutes at about room temperature, depending on the protecting groups selected; or, by incubating the solid support inside the reaction column used for the solid phase synthesis with 90% trifluoroacetic acid, 5% water and 5% triethylsilane for about 30 to 60 minutes. Other deprotection methods well known to those of skill in the art may also be used.

The polypeptides, i.e., ADNF polypeptides, of the present invention can be isolated and purified from the reaction mixture by means of peptide purification well known to those of skill in the art. For example, the polypeptides may be purified using known chromatographic procedures such as reverse phase HPLC, gel permeation, ion exchange, size exclusion, affinity, partition, or countercurrent distribution. See, the Example Section, infra, for a detailed description of the methods and protocols used to synthesize and purify the ADNF polypeptides of the present invention.

Although the ADNF polypeptides of the present invention are preferably prepared or produced using chemical peptide synthesis techniques such as described above, it will be understood by those of ordinary skill in the art that they can also be prepared by other means including, for example, recombinant techniques. Two text books which describe suitable recombinant techniques in great detail are Sambrook, et al., *Molecular Cloning, A Laboratory Manual* (Cold Spring Harbor Publish., Cold Spring Harbor, N.Y. 2nd ed. (1989)), *Methods in Enzymology*, Vol. 152: *Guide to Molecular Cloning Techniques* (Berger and Kimmel (eds.), San Diego: Academic Press, Inc. (1987)) and Kiegler, *Gene Transfer and Expression: A Laboratory Manual* (W. H. Freeman, N.Y. (1990)), the teachings of which are incorporated herein by reference.

In addition to the foregoing ADNF polypeptides which exhibit neuroprotective/neurotrophic activity, the present invention also provides an Activity Dependent Neurotrophic Factor (ADNF) polypeptide antagonist, the ADNF antagonist consisting essentially of the following amino acid sequence:

Ile-Pro-Ala-Leu-Asp-Ser-Leu-Lys-Pro-Ala-Asn-Glu-Asp-Gln-Lys-Ile-Gly-Ile-Glu-Ile(SEQ ID NO: 13).

Figure 10:
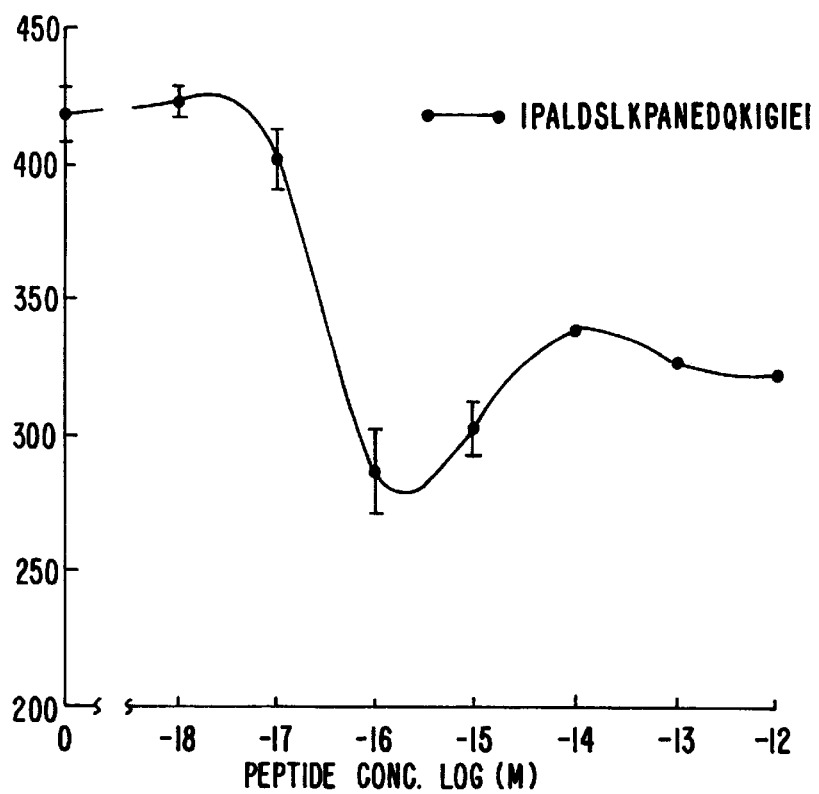
FIG. 10 illustrates that the ADNF/hsp60 antagonist produces neuronal cell death in dissociated cerebral cortical cultures (IPALDSLKPANEDQKIGIEI (SEQ ID NO: 13).

As shown in FIG. 10, this ADNF polypeptide antagonist produces neuronal cell death in cerebral cortical cultures (in this experiment, no tetrodoxtin was added to the test culture). As such, this ADNF polypeptide antagonist can be used to inhibit the activity of ADNF, thereby causing neuronal cell death. Such ADNF antagonists are particularly useful as controls to ensure that the results obtained in a given assay are derived from the activity of the ADNF polypeptide being tested and not from an artifact present in the assay system itself. Alternatively, such ADNF antagonists can be used to kill neuronal cells when it is desirable to specifically select for non-neuronal cells, such as in the isolation of ADNF. It should be noted that amino acid substitutions, additions, or deletions can be made to the sequence of the ADNF polypeptide antagonist set forth above provided they do not substantially alter the biological activity of that ADNF polypeptide antagonist. Moreover, the teachings regarding the synthesis and purification of the ADNF polypeptides described above are fully applicable to the synthesis and purification of this ADNF polypeptide antagonists.

C. Methods For Preventing Neuronal Cell Death Using Neurotrophic Polypeptides of ADNF In another aspect, the present invention provides a method for preventing neuronal cell death, the method comprising contacting the neuronal cells with an Activity Dependent Neurotrophic Factor (ADNF) polypeptide in an amount sufficient to prevent neuronal cell death, the ADNF polypeptide consisting essentially of the following amino acid sequence:

$(R^1)_x$-Ser-Ala-Leu-Leu-Arg-Ser-Ile-Pro-Ala-$(R^2)_y$(SEQ ID NO: 16)

With respect to the foregoing ADNF polypeptide, $R^1$, $R^2$, x and y have the same meanings as $R^1$, $R^2$, x and y in the previously described ADNF polypeptides (see, section B, supra) and, thus, the detailed descriptions of each substituent will not be provided again. Briefly, however, $R^1$ and $R^2$ are independently selected and are amino acid sequences comprising from 1 to about 40 amino acids wherein each amino acid is independently selected from the group consisting of naturally occurring amino acids and amino acid mimetics. Moreover, x and y are independently selected and are equal to zero or one. Further, $R^1$, $R^2$, x and y are selected such that the ADNF polypeptides of the present invention have other than the full length amino acid sequence of Activity Dependent Neurotrophic Factor.

As previously explained, the ADNF polypeptides of the present invention can be used in the treatment of neurological deficiencies and for the prevention of neuronal cell death. For example, such ADNF polypeptides can be used to prevent the death neuronal cells including, but not limited to, spinal cord neurons, hippocampal neurons, cerebral cortical neurons and cholingeric neurons. More particularly, the ADNF polypeptides of the present invention can be used in the prevention of cell death associated with (1) gp120, the envelope protein from HIV; (2) N-methyl-D-aspartic acid (excito-toxicity); (3) tetrodotoxin (blockage of electrical activity); and (4) beta-amyloid peptide, a substance related to neuronal degeneration in Alzheimer's disease. Each of the various methods of using the ADNF polypeptides of the present invention to prevent neuronal cell death or damage will be explained in greater detail hereinbelow. From these examples, it will be readily apparent to those of skill in the art that the ADNF polypeptides of the present invention can be used in a similar manner to prevent neuronal cell death associated with a number of other neurological diseases and deficiencies.

Figure 11:
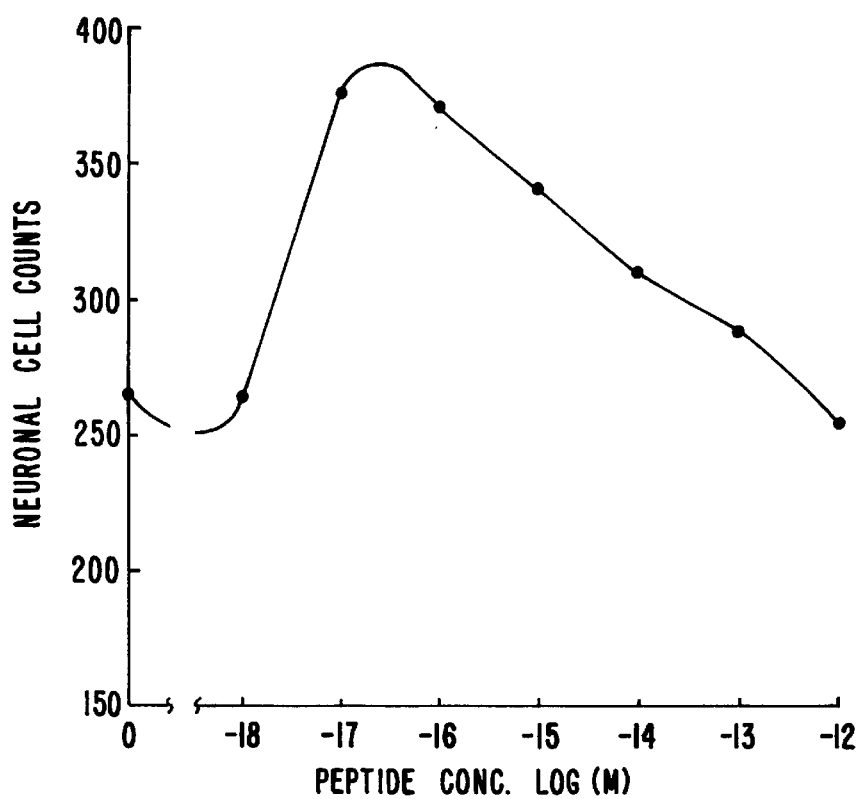
FIG. 11 illustrates the ability of an ADNF-related peptide (ADNF-14(SEQ ID NO: 1) to prevent neuronal cell death associated with the HIV envelope protein gp120.

Previous studies conducted with developing hippocampal neurons grown in cell culture have indicated that ADNF can prevent neuronal cell death associated with the external envelope protein of the HIV virus, i.e., gp120, the causative agent of AIDS (see, e.g., Brenneman, et al., Nature 335, 636 (1988), the teachings of which are hereby incorporated in their entirety by reference). It has now been discovered that the ADNF polypeptides of the present invention can also be used to prevent gp120-induced neuronal cell death. As shown in FIG. 11, ADNF-14, i.e., Val-Leu-Gly-Gly-Gly-Ser-Ala-Leu-Leu-Arg-Ser-Ile-Pro-Ala, (SEQ ID NO: 1) prevents neuronal cell death associated with 1 pM of the gp120 envelope protein of the HIV virus. Thus, by administering an effective amount of an ADNF polypeptide of the present invention to a patient infected with the HIV-1 virus, gp120-induced neuronal cell death can be prevented.

As such, in one aspect, the present invention provides a method for preventing neuronal cell death in a patient infected with human immunodeficiency virus, the method comprising administering to the patient an Activity Dependent Neurotrophic Factor (ADNF) polypeptide in an amount sufficient to prevent neuronal cell death and a pharmaceutically acceptable carrier, the ADNF polypeptide consisting essentially of the following amino acid sequence:

$(R^1)_x$-Ser-Ala-Leu-Leu-Arg-Ser-Ile-Pro-Ala-$(R^2)_y$. (SEQ ID NO: 16)

The previous discussion pertaining to $R^1$, $R^2$, x and y is fully applicable to the ADNF polypeptides used in this method of the present invention and, thus, will not be repeated with respect to this particular method. Within the scope of the above formula, certain ADNF polypeptides are preferred, namely those in which x and y are both zero (i.e., ADNF-9). Equally preferred are ADNF polypeptides in which x is one; $R^1$ is Val-Leu-Gly-Gly-Gly(SEQ ID NO: 15); and y is zero (i.e., ADNF-14). Also equally preferred are ADNF polypeptides in which x is one; $R^1$ is Val-Glu-Glu-Gly-Ile-Val-Leu-Gly-Gly-Gly; (SEQ ID NO: 20) and y is zero. It should be noted, however, that $R^1$, $R^2$, x and y are selected such that the ADNF polypeptides of the present invention have other than the full length amino acid sequence of Activity Dependent Neurotrophic Factor.

Moreover, it will be readily apparent to those of skill in the art that using the teachings set forth above with respect to the design and synthesis of ADNF polypeptides and the assay of Brenneman, et al., *Nature* 335,636 (1988), the teachings of which are hereby incorporated in their entirety by reference, one of ordinary skill in the art can identify other ADNF polypeptides which can be used to prevent cell death associated with gp120.

Figure 12:
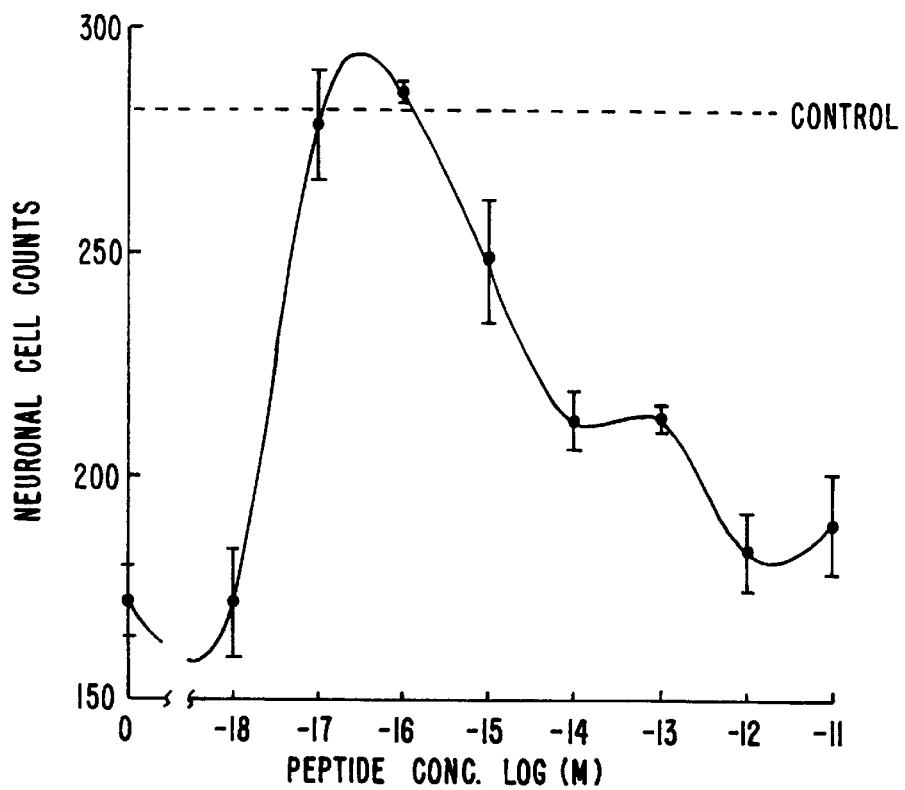
FIG. 12 illustrates the ability of an ADNF-related peptide to prevent neuronal cell death associated with NMDA toxicity in dissociated cerebral cortical cultures.

In addition to the foregoing, it has also been discovered that ADNF polypeptides can be used to prevent neuronal cell death associated with NMDA toxicity in dissociated cerebral cortical cultures (See, FIG. 12). As such, in another aspect, the present invention provides a method for preventing neuronal cell death associated with excito-toxicity induced by N-methyl-D-aspartate stimulation, the method comprising contacting these neuronal cells with an Activity Dependent Neurotrophic Factor (ADNF) polypeptide in an amount sufficient to prevent neuronal cell death, the ADNF polypeptide consisting essentially of the following amino acid sequence:

$(R^1)_x$-Ser-Ala-Leu-Leu-Arg-Ser-Ile-Pro-Ala-$(R^2)$. (SEQ ID NO: 16)

The prior discussions pertaining to $R^1$, $R^2$, x and y is fully applicable to the ADNF polypeptides used in this method of the present invention and, thus, it will not be repeated with respect to this particular method. Within the scope of the above formula, certain ADNF polypeptides are preferred, namely those in which x and y are both zero (i.e., ADNF-9). Equally preferred are ADNF polypeptides in which x is one; $R^1$ is Val-Leu-Gly-Gly-Gly(SEQ ID NO: 15); and y is zero (i.e., ADNF-14). Also equally preferred are ADNF polypeptides in which x is one; $R^1$ is Val-Glu-Glu-Gly-Ile-Val-Leu-Gly-Gly-Gly; (SEQ ID NO: 20) and y is zero. It should be noted, however, that $R^1$, $R^2$, x and y are selected such that the ADNF polypeptides of the present invention have other than the full length amino acid sequence of Activity Dependent Neurotrophic Factor.

Moreover, it will be readily apparent to those of skill in the art that using the teachings set forth above with respect to the design and synthesis of ADNF polypeptides and the assay of Brenneman, et al., *Dev. Brain Res.* 51:63 (1990), the teachings of which are hereby incorporated in their entirety by reference, one of ordinary skill in the art can identify other ADNF polypeptides which can be used to prevent cell death associated with excito-toxicity induced by stimulation by N-methyl-D-aspartate.

Figure 13:
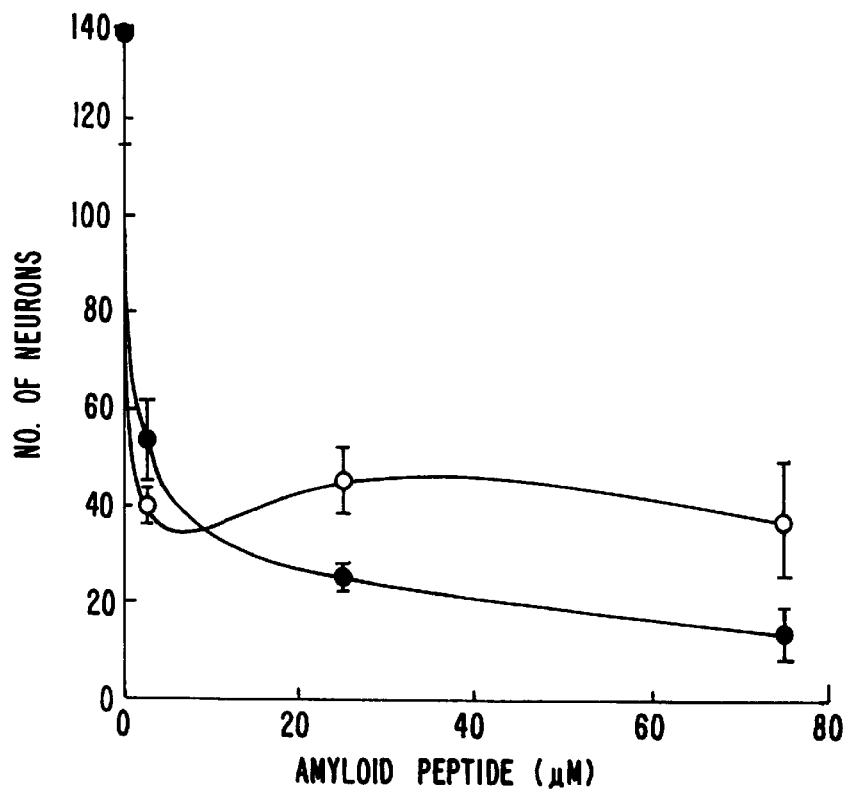
FIG. 13 illustrates the ability of the beta-amyloid peptide to induce neuronal cell death in dissociated cerebral cortical cultures.
Figure 14A:
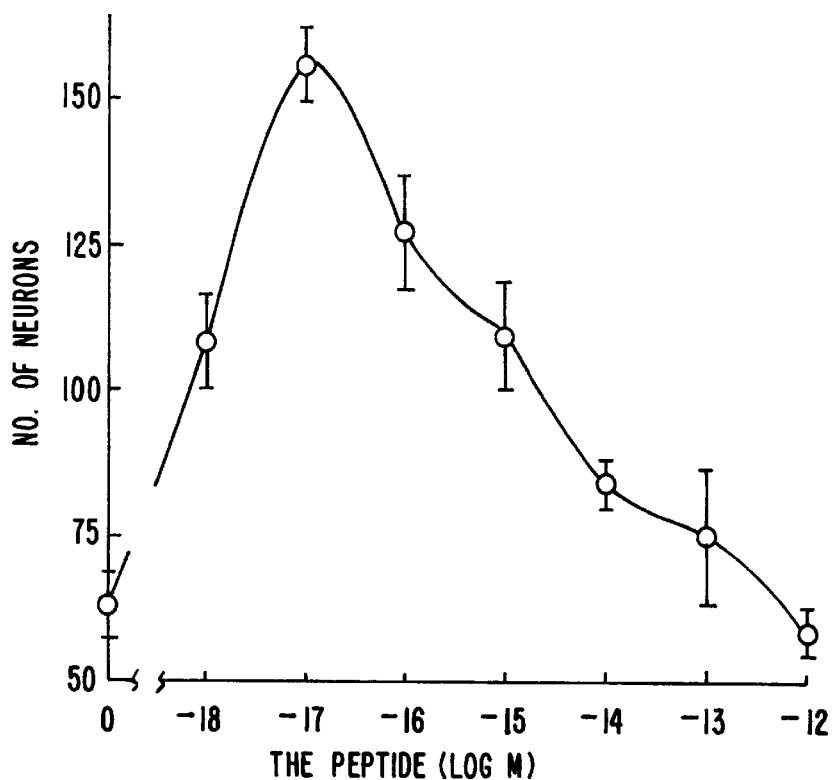
FIG. 14A illustrates that ADNF-14 can prevent cell death associated with beta-amyloid peptide, a causative agent in Alzheimer's disease.
Figure 14B:
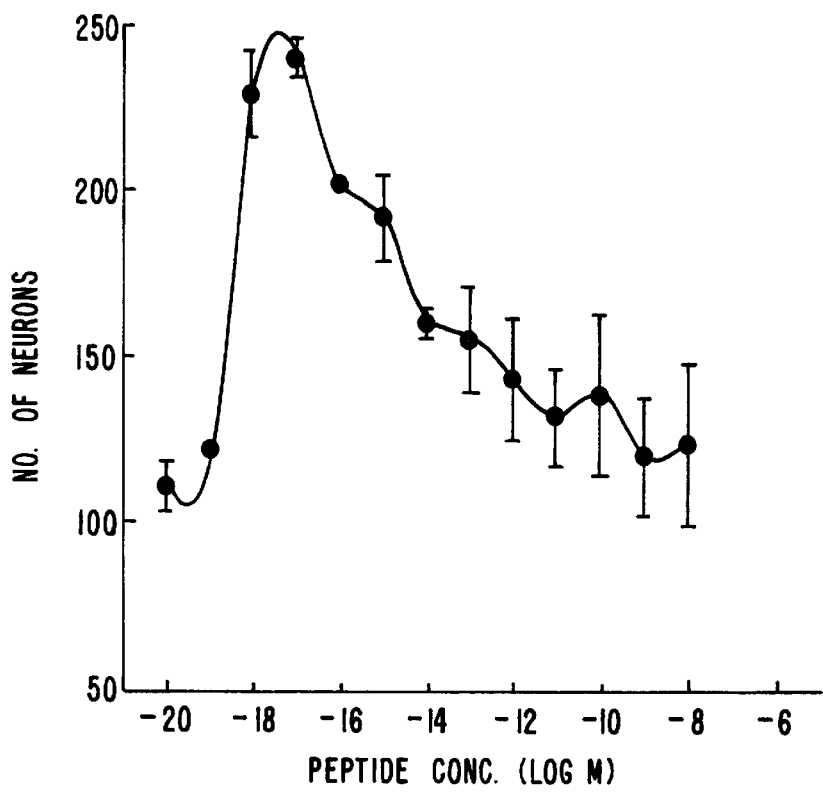
FIG. 14B illustrates that ADNF-9 can prevent cell death associated with beta-amyloid peptide, a causative agent in Alzheimer's disease.

In addition to the foregoing, it has also been discovered that the ADNF polypeptides of the present invention can prevent cell death associated with Alzheimer's disease (see, FIGS. 13, 14A and 14B). An in vitro model for Alzheimer's disease is offered by beta-amyloid neurotoxicity. The beta-amyloid peptide has been found to be deposited in Alzheimer's plaques (Kowall, et al., *Proc. Natl. Acad. Sci. USA* 88, 7247 (1991)), and has been suggested to have neurotoxic activity (Yankner, et al., *Science* 250, 279 (1990); Pike, et al., *J. Neurosci.* 13, 1676 (1993)). Accordingly, rat cerebral cortical cell cultures (as described above) were treated with increasing concentrations of a fragment of the beta-amyloid peptide (amino acids 25–35, synthesized as described, Gozes, et al., 90, 810 (1992); Gozes, et al., *Peptide Chemistry* 1992, N. Yanaihara Ed., 442–445 (1993) (ESCOM-Leiden); Gozes, et al., *Endocrinology* 134, 2121 (1994)). A five day incubation period with the fragment of the beta-amyloid peptide resulted in 70.5±0.5% neuronal cell death as compared to control (FIG. 13).

To evaluate the neuroprotective effects of ADNF-14 against beta-amyloid-associated death, ADNF-14 (initially dissolved in 20 µl acetonitrile and 180 µl water to a final concentration of $10^{-4}$M) was added with 25 µM of the beta-amyloid peptide fragment (as in FIG. 13). Results show that administration of the ADNF-14 peptide, i.e., Val-Leu-Gly-Gly-Gly-Ser-Ala-Leu-Leu-Arg-Ser-Ile-Pro-Ala(SEQ ID NO: 1) (denoted, "The Peptide" in the FIG. 14A), at fM concentrations and less, prevents beta-amyloid-related neuronal cell death in the tissue culture dish (See, FIG. 14A). Similarly, results show that administration of the ADNF-9 peptide, i.e., Ser-Ala-Leu-Leu-Arg-Ser-Ile-Pro-Ala, (SEQ ID NO: 2) at fM concentrations and less, prevents beta-amyloid-related neuronal cell death in the tissue culture dish (See, FIG. 14B).

As such, in another aspect, the present invention provides a method of preventing neuronal cell death induced by the beta-amyloid peptide in a patient afflicted or impaired with Alzheimer's disease, the method comprising administering to the patient an Activity Dependent Neurotrophic Factor (ADNF) polypeptide in an amount sufficient to prevent neuronal cell death and a pharmaceutically acceptable carrier, said ADNF polypeptide consisting essentially of the following amino acid sequence:

$(R^1)_x$-Ser-Ala-Leu-Leu-Arg-Ser-Ile-Pro-Ala-$(R^2)_y$. (SEQ ID NO: 16)

The prior discussions pertaining to $R^1$, $R^2$, x and y is fully applicable to the ADNF polypeptides used in this method of the present invention and, thus, it will not be repeated with respect to this particular method. Within the scope of the above formula, certain ADNF polypeptides are preferred, namely those in which x and y are both zero (i.e., ADNF-9). Equally preferred are ADNF polypeptides in which x is one; $R^1$ is Val-Leu-Gly-Gly-Gly(SEQ ID NO: 15); and y is zero (i.e., ADNF-14). Also equally preferred are ADNF polypeptides in which x is one; $R^1$ is Val-Glu-Glu-Gly-Ile-Val-Leu-Gly-Gly-Gly(SEQ ID NO: 20); and y is zero. It should be noted, however, that $R^1$, $R^2$, x and y are selected such that the ADNF polypeptides of the present invention have other than the full length amino acid sequence of Activity Dependent Neurotrophic Factor.

Moreover, it will be readily apparent to those of skill in the art that using the teachings set forth above with respect to the design and synthesis of ADNF polypeptides and the assay set forth above, one of ordinary skill in the art can identify other ADNF polypeptides which can be used to prevent cell death induced by the beta-amyloid peptide in a patient afflicted or impaired with Alzheimer's disease.

Figure 15A:
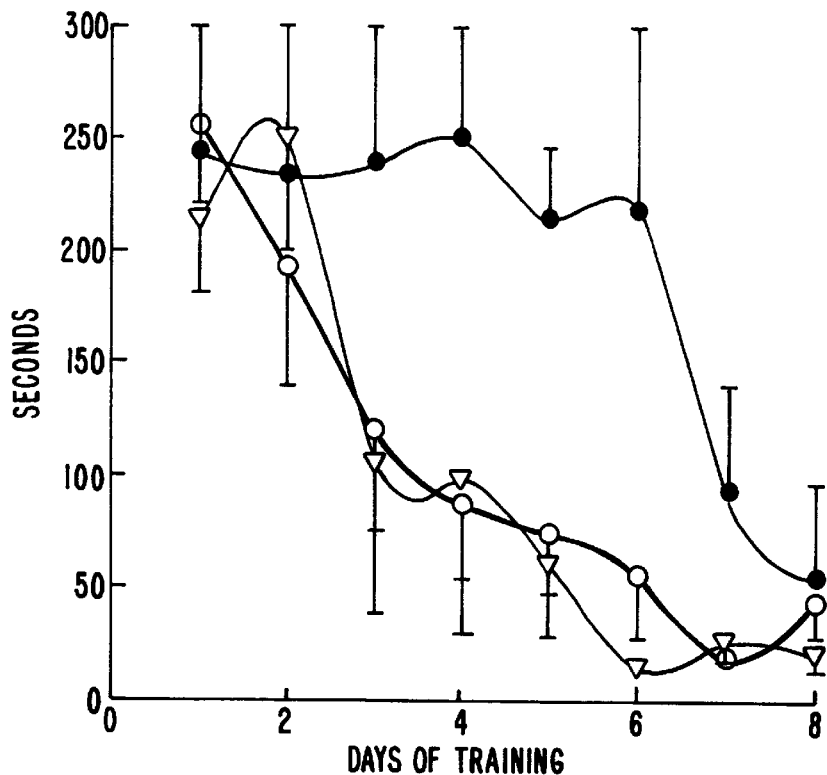
FIG. 15A illustrates that ADNF-14 can alleviate learning impairment produced by cholinergic blockade following daily nasal administration of 1 µg/day.
Figure 15B:
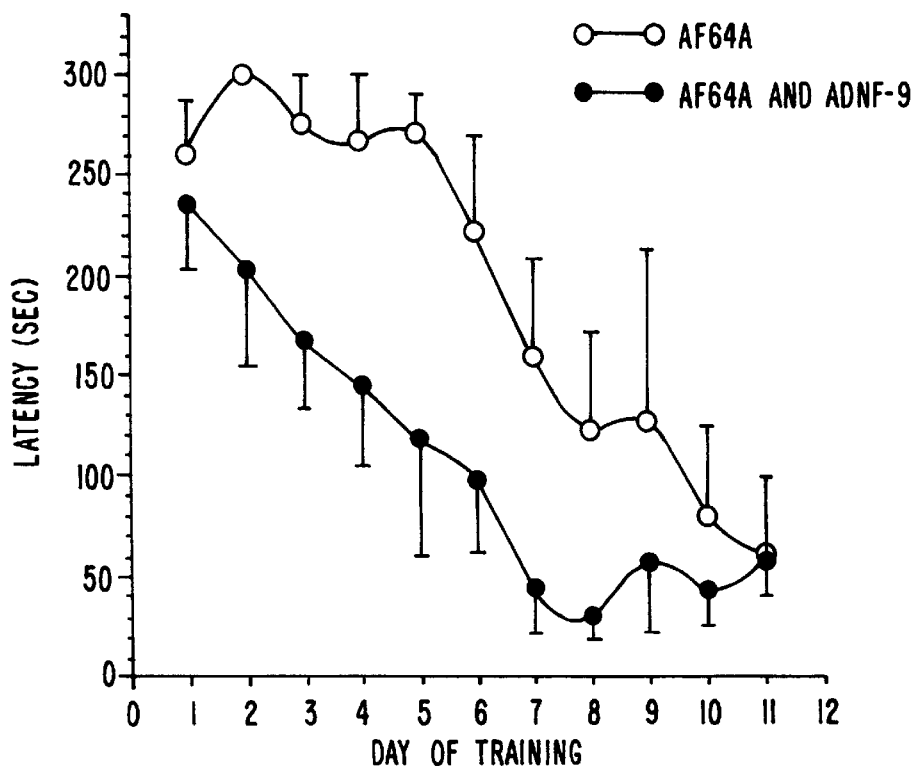
FIG. 15B illustrates that ADNF-9 can alleviate learning impairment produced by cholinergic blockade following daily nasal administration of 1 µg/day.

In addition to the foregoing, it has also been discovered that the ADNF. polypeptides of the present invention can alleviate learning impairment produced by cholinergic blockade. More particularly, as shown in FIG. 15A, it has now been discovered that ADNF-14 can alleviate learning impairment produced by cholinergic blockade following daily nasal administration of 1 µg/day. Similarly, as shown in FIG. 15B, it has now been discovered that ADNF-9 can alleviate learning impairment produced by cholinergic blockade following daily nasal administration of 1 µg/day. A system was adapted for in vivo evaluation of Alzheimer's-associated learning and memory deficits in rats. In humans suffering from Alzheimer's disease, there is an unexplained death of cholinergic neurons in the cerebral cortex and the hippocampus areas associated with cognitive functions of learning and memory. The cholinergic blocker AF64A produces learning and memory deficits typical of Alzheimer's disease (Fisher, et al., *Neurosci. Lett.* 102, 325 (1989)).

For the evaluation of learning and memory abilities, rats were tested in a Morris water maze as before (Morris, et al., Nature 297, 681 (1982); Morris, et al., Nature 319, 774 (1986); Glowa, et al., Brain Res., 570, 49 (1992); Gozes, et al., J. Mol. Neurosci., 4, 185 (1993). The latency of reaching the submerged platform in a circular water pool was recorded for each rat (in seconds) and the changes over days of training were graphed, which reflect learning and memory. Rats were injected with AF64A (i.c.v) at a rate of 0.21 μl/min., using plastic tubing (PE-20) attached to 25G needle; control animals receiving an injection of saline (2 μl/side); experimental animals receiving injections of AF64A (3 nmol/2μl/side) resulted in rats that did not learn even after 6 days of training (closed circles in FIG. 15A). Sham-treated controls (triangles in FIG. 15A) learned after 3 days of training. For peptide application the nasal route was chosen. Ten days after AF64A administration animals received daily nasal administration of the ADNF-14 dissolved in 10%sefsol (1-monocaproloyl-rac-glycerol) and 40% isopropanol at a concentration of 1 μg/40 ul (20 μl administered through each nostril). The animals were partially anesthetized by diethylether prior to nasal administration. The peptide was applied by nasal administration 1 hour prior to testing (ADNF-14, open circles in FIG. 15A). As shown in FIGS. 15A and 15B, ADNF-14 and ADNF-9, respectively, exhibits neuroprotective activity which is capable of ameliorating leaning deficiencies associated with cholinergic dysfunction.

As such, in still another aspect, the present invention provides a method of alleviating learning impairment produced by cholingeric blockage in a patient afflicted or impaired with Alzheimer's disease, the method comprising administering to the patient an Activity Dependent Neurotrophic Factor (ADNF) polypeptide in an amount sufficient to prevent neuronal cell death and a pharmaceutically acceptable carrier, the ADNF polypeptide consisting essentially of the following amino acid sequence:

(R$^1$)$_x$-Ser-Ala-Leu-Leu-Arg-Ser-Ile-Pro-Ala-(R$^2$). (SEQ ID NO: 16)

The prior discussions pertaining to R$^1$, R$^2$, x and y is fully applicable to the ADNF polypeptides used in this method of the present invention and, thus, will not be repeated with respect to this particular method. Within the scope of the above formula, certain ADNF polypeptides are preferred, namely those in which x and y are both zero (i.e., ADNF-9). Equally preferred are ADNF polypeptides in which x is one; R$^1$ is Val-Leu-Gly-Gly-Gly(SEQ ID NO: 15); and y is zero (i.e., ADNF-14). Also equally preferred are ADNF polypeptides in which x is one; R$^1$ is Val-Glu-Glu-Gly-Ile-Val-Leu-Gly-Gly-Gly(SEQ ID NO: 20); and y is zero. It should be noted, however, that R$^1$, R$^2$, x and y are selected such that the ADNF polypeptides of the present invention have other than the full length amino acid sequence of Activity Dependent Neurotrophic Factor.

Moreover, it will be readily apparent to those of skill in the art that using the teachings set forth above with respect to the design and synthesis of ADNF polypeptides and the assay set forth above, one of ordinary skill in the art can identify other ADNF polypeptides which can be used to alleviate leaning impairment produced by cholingeric blockage in a patient afflicted or impaired with Alzheimer's disease.

In still yet another aspect, the present invention provides pharmaceutical compositions comprising one of the previously described ADNF polypeptides in an amount sufficient to exhibit neuroprotective/neurotrophic activity, and a pharmaceutically acceptable diluent, carrier or excipient. The pharmaceutical compositions of the present invention are suitable for use in a variety of drug delivery systems. Suitable formulations for use in the present invention are found in Remington's Pharmaceutical Sciences (Mack Publishing Company, Philadelphia, Pa., 17th ed. (1985)), which is incorporated herein by reference. In addition, for a brief review of methods for drug delivery, see, Langer, Science 249:1527–1533 (1990), which is incorporated herein by reference.

Due to its ability to increase growth and survival of neurons, ADNF and ADNF polypeptides thereof have extensive uses in the treatment of neurological deficiencies which result, for example, from neuronal development, aging, neurodegenerative diseases or spinal cord injury. As such, the present invention provides for therapeutic compositions or medicaments comprising one or more of the ADNF polypeptides described hereinabove in combination with a pharmaceutically acceptable excipient, wherein the amount of the ADNF polypeptide is sufficient to provide a therapeutic effect.

In a therapeutic application, the ADNF polypeptides of the present invention are embodied in pharmaceutical compositions intended for parenteral, topical, oral or local administration. Preferably, the pharmaceutical compositions are administered parenterally, e.g., intravenously, subcutaneously, intradermally, or intramuscularly, or intranasally. Thus, the invention provides compositions for parenteral administration which comprise a solution of an ADNF polypeptide, as described above, dissolved or suspended in an acceptable carrier, preferably an aqueous carrier. A variety of aqueous carriers may be used including, for example, water, buffered water, 0.4% saline, 0.3% glycine, hyaluronic acid and the like. These compositions may be sterilized by conventional, well known sterilization techniques or, they may be sterile filtered. The resulting aqueous solutions may be packaged for use as is or lyophilized, the lyophilized preparation being combined with a sterile solution prior to administration. The compositions may contain pharmaceutically acceptable auxiliary substances as required to approximate physiological conditions including pH adjusting and buffering agents, tonicity adjusting agents, wetting agents and the like, such as, for example, sodium acetate, sodium lactate, sodium chloride, potassium chloride, calcium chloride, sorbitan monolaurate, triethanolamine oleate, etc.

For solid compositions, conventional nontoxic solid carriers may be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10–95% of active ingredient and more preferably at a concentration of 25%–75%.

For aerosol administration, the ADNF polypeptides are preferably supplied in finely divided form along with a surfactant and propellant. The surfactant must, of course, be nontoxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. A carrier can also be included, as desired, as with, e.g., lecithin for intranasal delivery.

In therapeutic applications, the ADNF polypeptides of the invention are administered to a patient in an amount sufficient to prevent neuronal cell death. An amount adequate to accomplish this is defined as "therapeutically effective dose." Amounts effective for this use will depend on, for example, the particular ADNF polypeptide employed, the type of neuronal cell death or damage to be prevented, the manner of administration, the weight and general state of health of the patient, and the judgment of the prescribing physician. For example, for the prevention of neuronal cell death, an amount of ADNF polypeptide falling within the range of a 100 ng to 10 mg dose given intranasally once a day (e.g., in the evening) would be a therapeutically effective amount.

The invention will be described in greater detail by way of specific examples. The following examples are offered for illustrative purposes, and are intended neither to limit or define the invention in any manner.

EXAMPLES

A. Isolation and Determination of ADNF:

Dose response of the survival-promoting activity of ADNF as determined by effects on spinal cord neurons: comparison between conditioned medium and purified ADNF. To isolate activity dependent factors, two different cell cultures were used. The source of the neurotrophic factors was rat cortical astrocytes, a superior source for astroglia because of rapid growth characteristics and established culture composition (McCarthy, K. D. & Partlow, L. M., *Brain Res.* 114, 391–414 (1976)). Two week old cultures (confluent 75cm$^2$ flasks) were washed three times with phosphate buffered saline (PBS) and conditioned medium was collected (10 ml PBS/flask) during a 3 hour incubation with 0.1 nM VIP (an amount previously shown to be optimal for releasing neurotrophic activity from astroglial cells, see, Brenneman, et al., *J. Neurosci. Res.* 25, 386–394 (1990)). The medium was centrifuged (3000× g for 10 min) and dialyzed (3.5 kdalton cutoff) against 50 mM sodium phosphate buffer, pH 7.0, 4° C.

The second type of cell culture, mouse spinal cord cultures, were used to test for biological activity of the conditioned medium. Dissociated mouse spinal cord cultures (obtained from 12-day old embryos) were plated (0.5 million cells/35 mm dish) in a medium consisting of 10% fetal calf serum and 10% heat-inactivated horse serum in minimal essential medium (MEM). After 24 hours, the medium was changed to 5% horse serum in MEM supplemented with defined-medium components (Romijn, et al., *Dev. Brain Res.* 2, 583–589 (1982)). Test cultures were treated for five days with varying amounts of conditioned medium in the presence of 1 $\mu$M tetrodotoxin. Neuronal cell counts were conducted after immunocytochemical identification with antiserum against neuronal specific enolase (Schmechel, et al., *Science* 199, 313–315 (1978)). Counts were made in 30 fields from pre-determined coordinate locations without knowledge of the treatment group. Each value is the mean of six determinations from three experiments (error bars are the SEM). The survival-promoting activity in unfractionated conditioned medium from astroglial cultures is depicted by triangles and the survival-promoting activity of purified ADNF by circles in FIG. 1. Purification details of ADNF are described infra.

B. Purification of ADNF:

Purification steps of ADNF as determined by effects on spinal cord neurons are set forth in FIG. 2. Spinal cord test cultures were treated as described above.

1. DEAE-Sephacel chromatography of VIP-stimulated astroglia-conditioned medium (See, FIG. 2A).

Dialyzed (50 mm sodium phosphate buffer, pH 7.0) conditioned medium (300 ml, 6–8 mg protein) was loaded onto a DEAE-Sephacel (Pharmacia AB Biotechnology Uppsala, Sweden) column (0.75 cm diameter and 3 cm length) pre-equilibrated with 50 mM sodium pyrophosphate buffer, pH 7.0. The column was washed sequentially with 40 ml of: 50 MM sodium pyrophosphate buffer (pH 7.0) and then the same buffer supplemented with increasing concentrations of NaCl: 0.1 M, 0.26 M, 0.5 M, 1.0 M, 2 M and 3 M. Column fractions, after dialysis against water (1:10,000), were added together with 1 $\mu$M tetrodotoxin to the spinal cord test cultures. Significant increases in neuronal cell counts were observed in the 2 M NaCl eluate. Results of neuronal cell counts (filled circles in FIG. 2A) are a mean of four determinations (error bars indicate SEM). The absorbance at 280 nm was determined after extensive dialysis against water, at 4° C., followed by lyophilization and solubilization in 1 ml water (open circles).

2. Size separation of the DEAE (2 M.NaCl eluate) activity dependent neurotrophic fraction on FPLC (See, FIG. 2B).

The 2 M NaCl fraction (corresponding to 300 ml original conditioned medium preparation) was dialyzed against water, lyophilized and resuspended in 0.5 ml of 50 mM sodium phosphate (pH 7.3) containing 0.15 M NaCl; 0.25 ml aliquots were loaded on Superose™12 column (prepacked HR 10/30), fast performance liquid chromatography (FPLC system, Pharmacia). Fractions (0.5 ml, 0.4 ml/min) were collected from the column, diluted with PBS (1:10,000) and tested in the neuronal survival assay. Significant increases in neuronal cell counts were observed in column fractions 22 and 31. Absorbance at 280 nm was determined as described above.

3. Purification of the low molecular weight neurotrophic activity by hydrophobic interaction FPLC (See, FIG. 2C).

Alkyl Superose™ (HR5/5, Pharmacia) column was washed with 0.1 M phosphate buffer (pH 7.0) and then equilibrated with 0.1 M phosphate buffer (pH 7.0) containing 2.0 M $(NH_4)_2SO_4$. The sample (0.5 ml of eluted fraction 31 from the size fractionation FPLC) was dialyzed extensively against deionized water, lyophilized and re-suspended in 0.1 M sodium phosphate buffer, pH 7.0 containing 1.43 M $(NH_4)_2SO_4$. Elution (1 ml fractions, 0.5 ml/min) was performed with a linear gradient of salt removal (2.0–0 M, depicted as dotted line) initiated 10 min after injection and lasting 60 min. Protein samples were dialyzed extensively against deionized water and analyzed for protein concentrations (Gozes, et al., *Endocrinol.* 134, 2121–2125 (1994)) using either immunoglobulins or bovine serum albumin as standards. After hydrophobic interaction chromatography, the amount of protein in the active fraction was determined by total amino acid analysis on a Beckman Model 7300 instrument following hydrolysis (24 hrs/110° C.) in 6N HCl containing 0.2% phenol. Samples eluted from the hydrophobic interaction column by salt removal were tested for biological activity and absorbance at 280 nm after dialysis against water. Results indicated that fraction 20 (0.94 to 1.04 M salt) contained the neurotrophic activity.

Figure 3A:
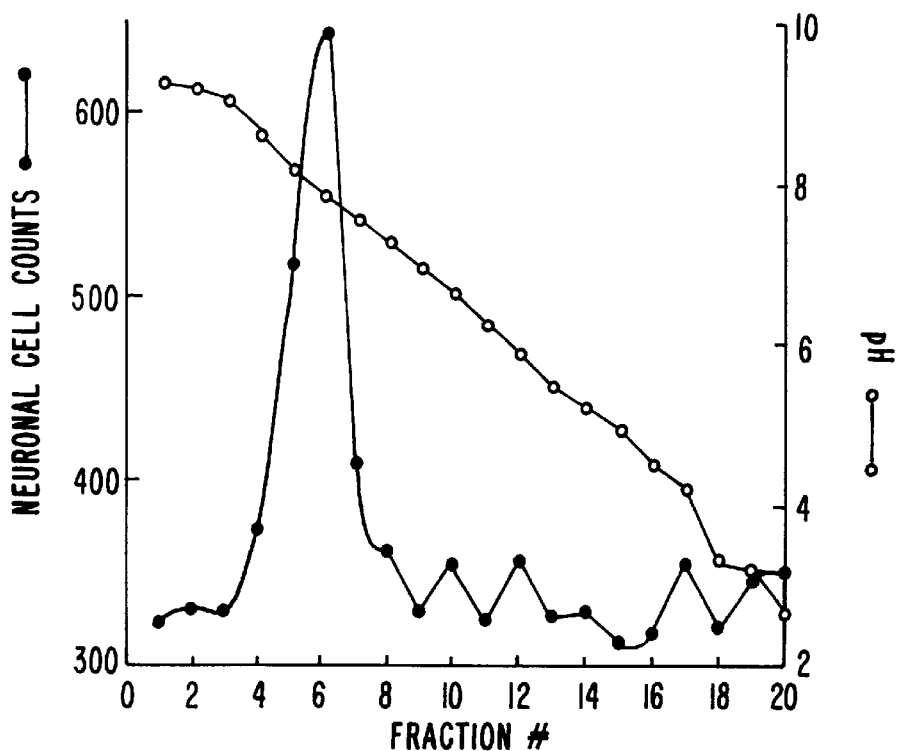
Figure 3B:
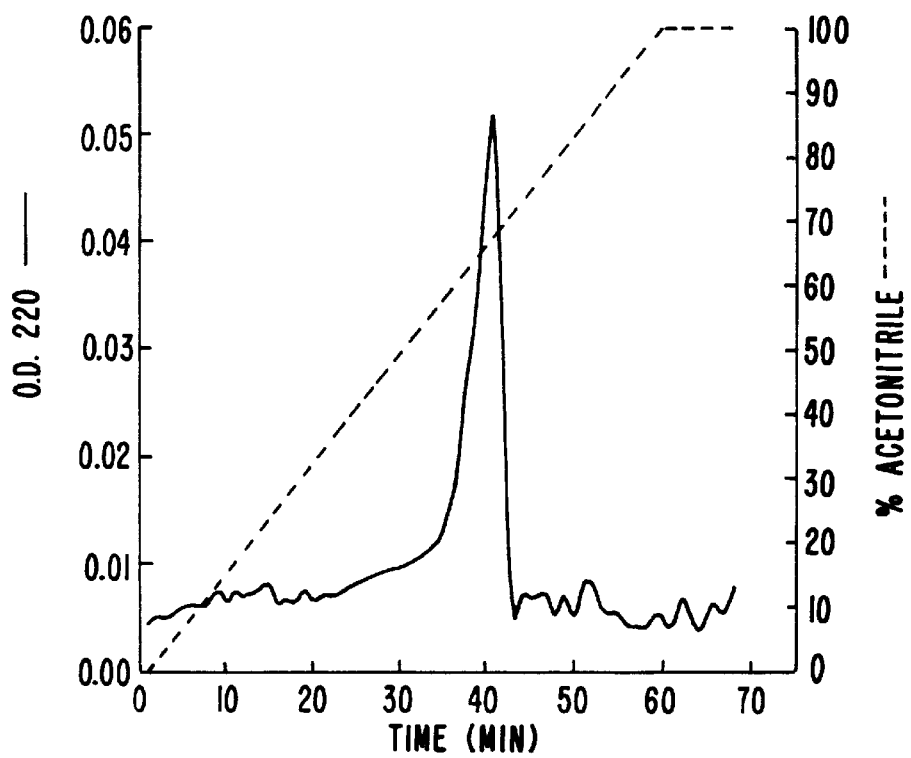

C. Biochemical Characteristics of Purified ADNF:

Purified ADNF (0.4 $\mu$g) was analyzed by isoelectric focusing using the MinipHor™ apparatus (See, FIG. 3A). Eluted fractions were assayed for survival-promoting activity after dilution 1:1000 with PBS. Each value is the mean of two closely agreeing (<10%) samples. The elution characteristics of ADNF displayed anomalous behavior in that isoelectric focusing techniques indicated the molecule was basic, whereas the elution profile after DEAE Sephacel suggested an acidic molecule; i.e., at neutral pH, the molecule eluted at very high salt concentration. Although the explanation for these observations is not yet clear, isoelectric separation techniques suggest that ADNF is basic and that the elution pattern off the ion exchange column reflects another property of the molecule such as hydrophobicity or highly charged microenvironments possibly resulting from protein assembly into macromolecular structures.

Following hydrophobic interaction chromatography, ADNF was analyzed by HPLC utilizing a LiChroCART 125–4, Lichrospher RP8, 5 microns Merck, Germany) (See, FIG. 3B). ADNF was solubilized in 2 ml of 50% acetonitrile containing 0.1% trifluoroacetic acid (TFA) and eluted with a gradient of 0–100% acetonitrile containing 0.1% TFA. ADNF was detected with an Applied Biosystems/AB 757 Absorbance Detector at a wave length of 220 nm with corrections made for baseline drift associated with the gradient. The protein peak also displayed biological activity when analyzed in a neuronal survival assay.

Purified ADNF (post reverse phase HPLC described in part 3B) was subjected to SDS-polyacrylamide gel electrophoresis on a 12% polyacrylamide SDS gel containing 0.1% SDS, according to Laemmli (*Nature* 227, 680–685 (1970)) (See, FIG. 3C). Gels were stained with silver stain (BioRad, Richmond, Calif.). Extraction of the 14,000 Daltons protein band from the polyacrylamide gel McManaman, et al., *J. Biol. Chem.* 12, 5890–5897 (1988)) resulted in an eluted protein which retained biological activity. Molecular weight determination was obtained by the parallel analysis of molecular weight markers.

D. Comparison of ADNF, ADNF-14 and A HSP60 Peptide For Survival-Promoting Activity ADNF, ADNF-14 and a hsp60 peptide were compared in terms of their survival-promoting activity in tetrodotoxin-treated cerebral cortical cultures (See, FIG. 4). ADNF is a survival-promoting protein that exhibits sequence homology to heat shock protein 60. Purified ADNF (open circles in FIG. 4) increased neuronal survival in comparison to cultures treated with tetrodotoxin alone at concentrations from $10^{16}$ to $10^{-12}$ M (P<0.001). ADNF-14 (i.e., VLGGGSALLRSIPA, open triangles in FIG. 4), a peptide derived from both sequence analysis of V8 protease digests of ADNF and homologous sequences of hsp6O, was found to exhibit identical potency and efficacy in comparison to intact ADNF. In contrast, the hsp 60 peptide homologue to ADNF-14 (VLGGGCALLRCIPA, (SEQ ID NO: 14) closed circles in FIG. 4) was less active, showing significant increases in survival in TTX-treated cultures at concentrations from $10^{-11}$ to $10^{-8}$ M (P<0.01) (See, Venner, T. J. & Gupta, R. S., *Nucleic Acid Res.* 18, 5309 (1990); and Peralta, et al., *Nucleic Acid Res.* 18, 7162 (1990)).

For peptide sequencing, HPLC-eluted ANDF (3–5 μg) was subjected to V8 protease digestion (Boehringer Mannheim). The reaction was carried out in 50 mM ammonium hydrogen carbonate, pH 7.8 with an enzyme to substrate ratio of 1:50 at 37° C. for 16 hours. Resulting peptides were resolved by HPLC chromatography (as described above). Peptides were sequenced on Model 470 and 477 Applied Biosystems Inc. Peptides were dried onto Biobrene-coated cartridge filters (Applied Biosystems, Inc.), and the tube that contained the peptide was rinsed with 30 μl of trifluoroacetic acid which was also dried on top of the filter.

Peptides were synthesized according to solid phase strategy employing optimum side chain protection (Gozes, et al., *Endocrinol.* 134, 2121–2125 (1994)). Products were purified on Sephadex G-25 and reversed phase HPLC. Peptides showed the desired molar ratios of amino acids that are consistently present in the synthesized peptides. Survival assays were conducted in test cultures as described (Hill, et al., *Brain Res.* 603, 222–233 (1993)). Seven days after neuronal seeding, cultures were treated for a five day test period. Neurons were counted as previously described (Brenneman, et al., *Dev. Brain Res.* 15, 211–217 (1984)) without knowledge of the treatment group.

E. Ability of ADNF To Incorporate Thymidine into DNA

Figure 16:
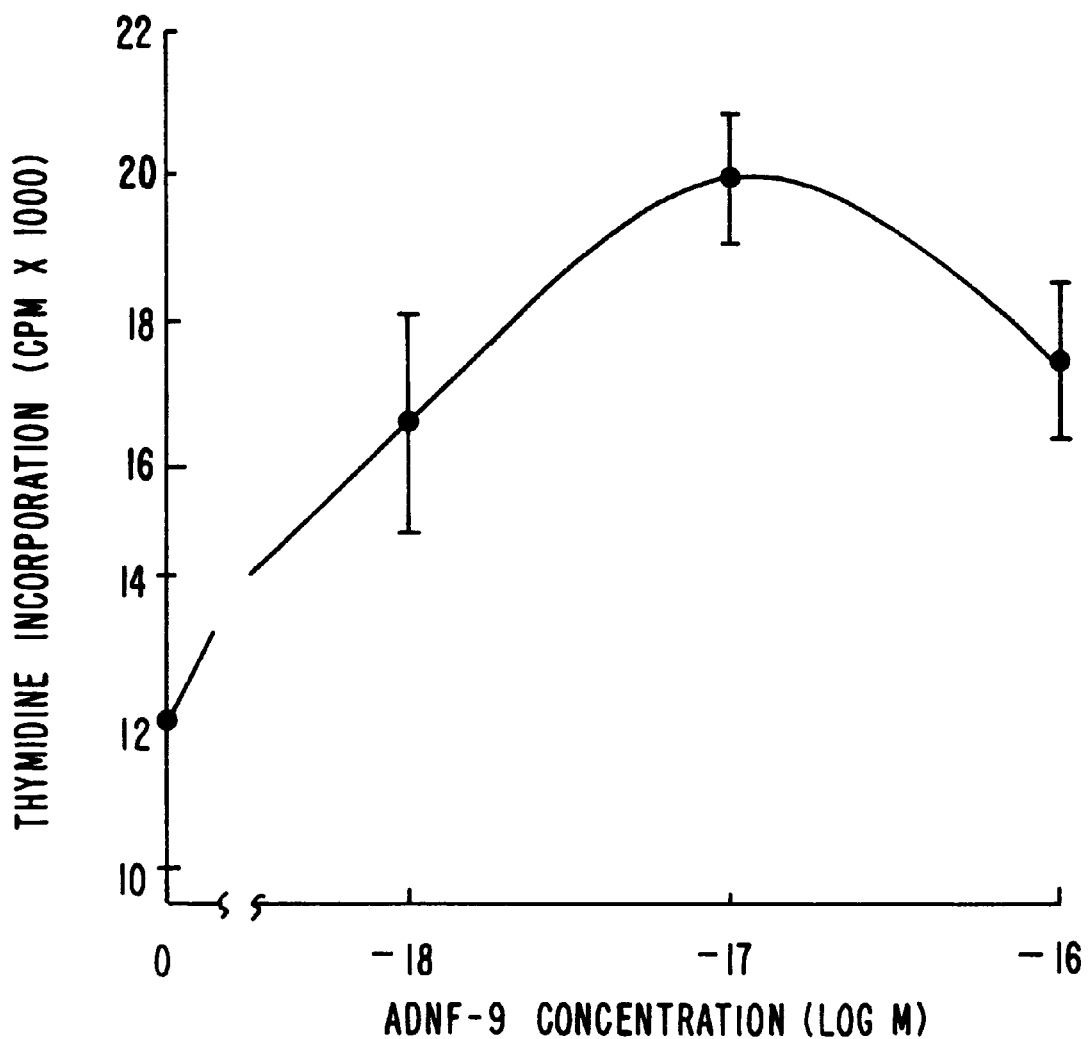
FIG. 16 illustrates that ADNF-9 increases thymidine incorporation into DNA of human neuroblastoma.

ADNF-9 has now been found to stimulate the incorporation of thymidine into DNA of human neuroblastoma (see, FIG. 16). The ability to incorporate thymidine into DNA is used as a biological measure of cell proliferation. The cell line used for these experiments is a neuroblastoma derived from human tissue. The NMB human neuroblastoma cell line was grown for 24 hours and then treated with various concentrations of ADNF-9. Tritiated thymidine was added at the time of ADNF-9 treatment. The duration of treatment was 24 hours. The assay and cell culture concentrations were done previously as described in Wollman, et al., *Brain Res.* 624, 339 (1993). Each point set forth in FIG. 17 is the mean±the standard error of 4–5 determinations. From these data, it is readily apparent that ADNF-9 has the ability to stimulate the incorporation of thymidine into DNA.

All publications mentioned hereinabove are hereby incorporated in their entirety by reference.

The foregoing is offered for purposes of illustration. It will be readily apparent to those skilled in the art that the operating conditions, materials, procedural steps and other parameters of the methods and test devices described herein may be further modified or substituted in ways without departing from the spirit and scope of the invention.

What is claimed is:

1. An Activity Dependent Neurotrophic Factor (ADNF) polypeptide that promotes survival of rat cortical neurons in vitro, said polypeptide consisting of the following amino acid sequence:

$(R^1)_x$-Ser-Ala-Leu-Leu-Arg-Ser-Ile-Pro-Ala-$(R^2)_y$(SEQ ID NO: 16)

in which:
  $R^1$ is an amino acid sequence consisting of from 1 to 40 amino acids wherein each amino acid is independently selected from the group consisting of naturally occurring amino acids and amino acid mimetics;
  $R^2$ is an amino acid sequence consisting from 1 to 40 amino acids wherein each amino acid is independently selected from the group consisting of naturally occurring amino acids and amino acid mimetics; and
  x and y are independently selected and are equal to zero or one.

2. The Activity Dependent Neurotrophic Factor polypeptide in accordance with claim 1 wherein:
  x and y are both zero.

3. The Activity Dependent Neurotrophic Factor polypeptide in accordance with claim 1 wherein:
  x is one;
  $R^1$ is Val-Leu-Gly-Gly-Gly(SEQ ID NO: 15); and
  y is zero.

4. The Activity Dependent Neurotrophic Factor polypeptide in accordance with claim 1 wherein:
  x is one;
  $R^1$ is Val-Glu-Glu-Gly-Ile-Val-Leu-Gly-Gly-Gly(SEQ ID NO: 20); and
  y is zero.

5. An Activity Dependent Neurotrophic Factor (ADNF) polypeptide antagonist, said antagonist comprising the following amino acid sequence:

Ile-Pro-Ala-Leu-Asp-Ser-Leu-Lys-Pro-Ala-Asn-Glu-Asp-Gln-Lys-Ile-Gly-Ile-Glu-Ile (SEQ ID NO: 13);

provided that:
  said ADNF polypeptide antagonist has other than the full length amino acid sequence of heat shock protein 60 (hsp60).

6. A method for reducing neuronal cell death, said method comprising contacting said neuronal cells with an Activity Dependent Neurotrophic Factor (ADNF) polypeptide in an amount sufficient to reduce neuronal cell death, said ADNF polypeptide consisting of the following amino acid sequence:

$(R^1)_x$-Ser-Ala-Leu-Leu-Arg-Ser-Ile-Pro-Ala-$(R^2)_y$(SEQ ID NO: 16)

in which:
  $R^1$ is an amino acid sequence consisting of from 1 to 40 amino acids wherein each amino acid is independently selected from the group consisting of naturally occurring amino acids and amino acid mimetics;
  $R^2$ is an amino acid sequence consisting of from 1 to 40 amino acids wherein each amino acid is independently selected from the group consisting of naturally occurring amino acids and amino acid mimetics; and
  x and y are independently selected and are equal to zero or one.

7. The method in accordance with claim 6 wherein said neuronal cells are selected from the group consisting of spinal cord neurons, hippocampal neurons, cerebral cortical neurons and cholinergic neurons.

8. The method in accordance with claim 6 wherein:
  x and y are both zero.

9. The method in accordance with claim 6 wherein:
  x is one;
  $R^1$ is Val-Leu-Gly-Gly-Gly(SEQ ID NO: 15); and
  y is zero.

10. The method in accordance with claim 6 wherein:
x is one;
R¹ is Val-Glu-Glu-Gly-Ile-Val-Leu-Gly-Gly-Gly(SEQ ID NO: 20); and
y is zero.

11. A method for reducing gp120 induced neuronal cell death in a patient infected with human immunodeficiency virus, said method comprising administering to said patient an Activity Dependent Neurotrophic Factor (ADNF) polypeptide in an amount sufficient to reduce gp120 induced neuronal cell death and a pharmaceutically acceptable carrier, said ADNF polypeptide consisting of the following amino acid sequence:

$(R^1)_x$-Ser-Ala-Leu-Leu-Arg-Ser-Ile-Pro-Ala-$(R^2)_y$(SEQ ID NO: 16)

in which:
R¹ is an amino acid sequence consisting of from 1 to 40 amino acids wherein each amino acid is independently selected from the group consisting of naturally occurring amino acids and amino acid mimetics;
R² is an amino acid sequence consisting of from 1 to 40 amino acids wherein each amino acid is independently selected from the group consisting of naturally occurring amino acids and amino acid mimetics; and
x and y are independently selected and are equal to zero or one.

12. The method in accordance with claim 11 wherein:
x and y are both zero.

13. The method in accordance with claim 11 wherein:
x is one;
R¹ is Val-Leu-Gly-Gly-Gly(SEQ ID NO: 15); and
y is zero.

14. A method for reducing neuronal cell death associated with excito-toxicity induced by N-methyl-D-aspartate stimulation, said method comprising contacting said neuronal cells with an Activity Dependent Neurotrophic Factor (ADNF) polypeptide in an amount sufficient to reduce N-methyl-D-aspartate induced neuronal cell death, said ADNF polypeptide consisting of the following amino acid sequence:

$(R^1)_x$-Ser-Ala-Leu-Leu-Arg-Ser-Ile-Pro-Ala-$(R^2)_y$(SEQ ID NO: 16)

in which:
R¹ is an amino acid sequence consisting of from 1 to 40 amino acids wherein each amino acid is independently selected from the group consisting of naturally occurring amino acids and amino acid mimetics;
R² is an amino acid sequence consisting of from 1 to 40 amino acids wherein each amino acid is independently selected from the group consisting of naturally occurring amino acids and amino acid mimetics; and
x and y are independently selected and are equal to zero or one.

15. The method in accordance with claim 14 wherein:
x and y are both zero.

16. The method in accordance with claim 14 wherein:
x is one;
R¹ is Val-Leu-Gly-Gly-Gly(SEQ ID NO: 15); and
y is zero.

17. A method of reducing neuronal cell death induced by the beta-amyloid peptide in a patient afflicted with Alzheimer's disease, said method comprising administering to said patient an Activity Dependent Neurotrophic Factor (ADNF) polypeptide in an amount sufficient to reduce beta-amyloid peptide induced neuronal cell death and a pharmaceutically acceptable carrier, said ADNF polypeptide consisting of the following amino acid sequence:

$(R^1)_x$-Ser-Ala-Leu-Leu-Arg-Ser-Ile-Pro-Ala-$(R^2)_y$(SEQ ID NO: 16)

in which:
R¹ is an amino acid sequence consisting of from 1 to 40 amino acids wherein each amino acid is independently selected from the group consisting of naturally occurring amino acids and amino acid mimetics;
R² is an amino acid sequence consisting of from 1 to 40 amino acids wherein each amino acid is independently selected from the group consisting of naturally occurring amino acids and amino acid mimetics; and
x and y are independently selected and are equal to zero or one.

18. The method in accordance with claim 17 wherein:
x and y are both zero.

19. The method in accordance with claim 17 wherein:
x is one;
R¹ is Val-Leu-Gly-Gly-Gly(SEQ ID NO: 15); and
y is zero.

20. A method of alleviating learning impairment produced by cholingeric blockage in a patient afflicted with Alzheimer's disease, said method comprising administering to said patient an Activity Dependent Neurotrophic Factor (ADNF) polypeptide in an amount sufficient to alleviate learning impairment produced by cholinergic blockade and a pharmaceutically acceptable carrier, said ADNF polypeptide consisting of the following amino acid sequence:

$(R^1)_x$-Ser-Ala-Leu-Leu-Arg-Ser-Ile-Pro-Ala-$(R^2)_y$(SEQ ID NO: 16)

in which:
R¹ is an amino acid sequence consisting of from 1 to 40 amino acids wherein each amino acid is independently selected from the group consisting of naturally occurring amino acids and amino acid mimetics;
R² is an amino acid sequence consisting of from 1 to 40 amino acids wherein each amino acid is independently selected from the group consisting of naturally occurring amino acids and amino acid mimetics; and
x and y are independently selected and are equal to zero or one.

21. The method in accordance with claim 20 wherein:
x and y are both zero.

22. The method in accordance with claim 20 wherein:
x is one;
R¹ is Val-Leu-Gly-Gly-Gly(SEQ ID NO: 15); and
y is zero.

23. A method for inducing neuronal cell death, said method comprising contacting said neuronal cells with an Activity Dependent Neurotrophic Factor (ADNF) polypeptide antagonist in an amount sufficient to induce neuronal cell death, said ADNF polypeptide antagonist comprising the following amino acid sequence:
Ile-Pro-Ala-Leu-Asp-Ser-Leu-Lys-Pro-Ala-Asn-Glu-Asp-Gln-Lys-Ile-Gly-Ile-Glu-Ile(SEQ ID NO: 13).

24. A pharmaceutical composition comprising a pharmaceutically acceptable excipient and an Activity Dependent Neurotrophic Factor (ADNF) polypeptide that promotes survival of rat cortical neurons in vitro, said ADNF polypeptide consisting of the following amino acid sequence:

($R^1$)$_x$-Ser-Ala-Leu-Leu-Arg-Ser-Ile-Pro-Ala-($R^2$)$_y$(SEQ ID NO: 16)

in which:
  $R^1$ is an amino acid sequence consisting of from 1 to 40 amino acids wherein each amino acid is independently selected from the group consisting of naturally occurring amino acids and amino acid mimetics;
  $R^2$ is an amino acid sequence consisting of from 1 to 40 amino acids wherein each amino acid is independently selected from the group consisting of naturally occurring amino acids and amino acid mimetics; and
  x and y are independently selected and are equal to zero or one.

25. An Activity Dependent Neurotrophic Factor (ADNF) according to claim 24, wherein:
  x is one;
  $R^1$ is Val-Leu-Gly-Gly-Gly (SEQ ID NO: 15); and
  y is zero.

26. An Activity Dependent Neurotrophic Factor (ADNF) according to any one of claims 1 or 24, wherein:
  x is one;
  $R^1$ is selected from the group consisting of:
    (a) Leu-Gly-Gly-Gly;
    (b) Gly-Gly-Gly;
    (c) Gly-Gly; and
    (d) Gly; and
  y is zero.

27. An Activity Dependent Neurotrophic Factor (ADNF) according to claim 26, wherein:
  X is one;
  $R^1$ is Leu-Gly-Gly-Gly; and
  y is zero.

28. Activity Dependent Neurotrophic Factor (ADNF) according to claim 26, wherein:
  X is one;
  $R^1$ is Gly-Gly-Gly; and
  y is zero.

29. An Activity Dependent Neurotrophic Factor (ADNF) according to claim 26, wherein:
  X is one;
  $R^1$ is Gly-Gly; and
  y is zero.

30. An Activity Dependent Neurotrophic Factor (ADNF) according to claim 26, wherein:
  X is one;
  $R^1$ is Gly; and
  y is zero.

31. The method according to any one of claims 6, 11, 14, 17, or 20, wherein:
  x is one;
  $R^1$ is selected from the group consisting of:
    (a) Leu-Gly-Gly-Gly;
    (b) Gly-Gly-Gly;
    (c) Gly-Gly; and
    (d) Gly; and
  y is zero.

32. The method according to claim 31, wherein:
  X is one;
  $R^1$ is Leu-Gly-Gly-Gly; and
  y is zero.

33. The method according to claim 31, wherein:
  X is one;
  $R^1$ is Gly-Gly-Gly; and
  y is zero.

34. The method according to claim 31, wherein:
  X is one;
  $R^1$ is Gly-Gly; and
  y is zero.

35. The method according to claim 31, wherein:
  X is one;
  $R^1$ is Gly; and
  y is zero.

* * * * *

UNITED STATES PATENT AND TRADEMARK OFFICE
CERTIFICATE OF CORRECTION

PATENT NO. : 6,174,862 B1
DATED : January 16, 2001
INVENTOR(S) : Douglas E. Brenneman and Illana Gozes Page 1 of 1

It is certified that error appears in the above-identified patent and that said Letters Patent is hereby corrected as shown below:

<u>Title page,</u>
Item [12], after "Brenneman", please insert -- et al. --
Item [75], after "(US)", please insert -- Illana Gozes, Hasharon, Israel --

Signed and Sealed this

Twelfth Day of March, 2002

*Attest:*

*Attesting Officer*

JAMES E. ROGAN
*Director of the United States Patent and Trademark Office*